US010839940B2

(12) United States Patent
Mishra et al.

(10) Patent No.: US 10,839,940 B2
(45) Date of Patent: Nov. 17, 2020

(54) METHOD, COMPUTER-ACCESSIBLE MEDIUM AND SYSTEMS FOR SCORE-DRIVEN WHOLE-GENOME SHOTGUN SEQUENCE ASSEMBLE

(75) Inventors: Bhubaneswar Mishra, Great Neck, NY (US); Giuseppe Narzisi, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 13/139,809

(22) PCT Filed: Dec. 23, 2009

(86) PCT No.: PCT/US2009/069509
§ 371 (c)(1),
(2), (4) Date: Oct. 26, 2011

(87) PCT Pub. No.: WO2010/075570
PCT Pub. Date: Jul. 1, 2010

(65) Prior Publication Data
US 2012/0041727 A1 Feb. 16, 2012

Related U.S. Application Data

(60) Provisional application No. 61/140,831, filed on Dec. 24, 2008.

(51) Int. Cl.
*G16B 30/20* (2019.01)
(52) U.S. Cl.
CPC .................................. *G16B 30/20* (2019.02)
(58) Field of Classification Search
None
See application file for complete search history.

(56) References Cited

U.S. PATENT DOCUMENTS 6,221,592 B1  4/2001  Schwartz et al.
2006/0155483 A1* 7/2006  Antoniotti et al. ............. 702/20

FOREIGN PATENT DOCUMENTS

WO    WO 2008/112754    9/2008

OTHER PUBLICATIONS

Aston, C., Mishra, B. & Schwartz, D. C. Optical mapping and its potential for large-scale sequencing projects. Trends in Biotechnology 17, 297-302 (1999).*

(Continued)

*Primary Examiner* — Soren Harward
(74) *Attorney, Agent, or Firm* — Hunton Andrews Kurth LLP

(57) ABSTRACT

Exemplary embodiments of the present disclosure relate generally to methods, computer-accessible medium and systems for assembling haplotype and/or genotype sequences of at least one genome, which can be based upon, e.g., consistent layouts of short sequence reads and long-range genome related data. For example, a processing arrangement can be configured to perform a procedure including, e.g., obtaining randomly located short sequence reads, using at least one score function in combination with constraints based on, e.g., the long range data, generating a layout of randomly located short sequence reads such that the layout is globally optimal with respect to the score function, obtained through searching coupled with score and constraint dependent pruning to determine the globally optimal layout substantially satisfying the constraints, generating a whole and/or a part of a genome wide haplotype sequence and/or genotype sequence, and converting a globally optimal layout into one or more consensus sequences.

63 Claims, 12 Drawing Sheets

(56) References Cited

OTHER PUBLICATIONS

Błażewicz, J., Formanowicz, P. & Kasprzak, M. Selected combinatorial problems of computational biology. European Journal of Operational Research 161, 585-597 (2005).*
Goldberg, S. M. D. et al. A Sanger/pyrosequencing hybrid approach for the generation of high-quality draft assemblies of marine microbial genomes. Proceedings of the National Academy of Sciences USA 103, 11240-11245 (2006).*
Li, M., Nordborg, M. & Li, L. M. Adjust quality scores from alignment and improve sequencing accuracy. Nucleic acids research 32, 5183-91 (2004).*
Lippert, R., Schwartz, R., Lancia, G. & Istrail, S. Algorithmic strategies for the single nucleotide polymorphism haplotype assembly problem. Briefings in Bioinformatics 3, 23-31 (2002).*
Pesant, G., Gendreau, M., Potvin, J.-Y. & Rousseau, J.-M. An Exact Constraint Logic Programming Algorithm for the Traveling Salesman Problem with Time Windows. Transportation Science 32, 12-29 (1998).*
Pesant, G., Gendreau, M., Potvin, J.-Y. & Rousseau, J.-M. On the flexibility of constraint programming models: From single to multiple time windows for the traveling salesman problem. European Journal of Operational Research 117, 253-263 (1999).*
Zhou, S. et al. Whole-genome shotgun optical mapping of Rhodobacter sphaeroides strain 2.4.1 and its use for whole-genome shotgun sequence assembly. Genome Research 13, 2142-2151 (2003).*
Nagarajan, N., Read, T. D. & Pop, M. Scaffolding and validation of bacterial genome assemblies using optical restriction maps. Bioinformatics 24, 1229-1235 (2008).*
Dorigo, M. & Stützle, T. in Handbook of Metaheuristics (Dorigo, M. & Stützle, T.) 250-285 (Springer, 2003).*
Meksangsouy, P. & Chaiyaratana, N. DNA fragment assembly using an ant colony system algorithm. in Congress on Evolutionary Computation 3, 1756-1763 (IEEE, 2003).*
Sundquist, A., Ronaghi, M., Tang, H., Pevzner, P. & Batzoglou, S. Whole-genome sequencing and assembly with high-throughput, short-read technologies. PLoS One 2, e484 (2007).*
Sutton, G. G., White, O., Adams, M. D. & Kerlavage, A. R. TIGR Assembler: A New Tool for Assembling Large Shotgun Sequencing Projects. Genome Science and Technology 1, 9-19 (1995).*
Camerini, P. M., Fratta, L. & Maffioli, F. The K Best Spanning Arborescences of a Network. Networks 10, 91-109 (1980).*
International Search Report for the International Application No. PCT/US2009/069509 dated Sep. 6, 2010.
Written Opinion for the International Application No. PCT/US2009/069509 dated Sep. 6, 2010.
Adam M. Phillippy et al., "Genome assembly forensics: finding the elusive mis-assembly," Genome Biology, Mar. 2008, vol. 9, Issue 3, Article R55.
J.D. Kececioglu et al., "Combinatorial Algorithms for DNA Sequence Assembly," Algorithmica, 1995, vol. 13, No. 1-2, pp. 7-51.
Scott C.—H. et al., "Shotgun: Getting more from sequence similarity searches," Bioinformatics, Sep. 1999, vol. 15, No. 9, pp. 729-740.
D.Y. Lin et al., "Likelihood-Based Inference on Haplotype Effects in Genetic Association Studies," Journal of the American Statistical Association, Mar. 2006, vol. 101, No. 473, pp. 89-104.
Mukund Sundararajan et al., "Chaining Algorithms for Alignment of Draft Sequence," Algorithms in Bioinformatics, Sep. 2004, vol. 3240/2004, pp. 326-337.
Smith, L.M. et al."Fluorescence Detection in Automated DNA Sequence Analysis," Nature, 321(6071);674-679,1986.
Nyren,P. etal.,"Solid Phase DNA Mini sequencing by an Enzymatic Luminometric Inorganic Pyrophosphate Detection Assay," Annual Biochem208(1):171-175, 1993.
Ronaghi, M. et al., "PCR-Introduced Loop Structure as Primer in DNA sequencing," Biotechniques, 25(5):876-884,1998.
Margulies, M. et al., "Genome Sequencing in Micro¬ fabricated High-Density Picoliter Reactors," Nature,437(7057):376-380,2005.
L .Feuk, et al. "Structural. Variation in the Human Genome," Nature Review Genetics,7(2): 85-97,2006.
Barany,F.,"The Ligase Chain Reaction in aPCR World," PCR Methods Appl.,1(1): 5-16, 1991.
Nickerson, D.A., et al., "Automated DNA Diagnostics Using an ELISA-Based Oligonucleotide Ligation Assay," PNAS,87(22);8923-8927,1991.
Drmanac, R.,etal., "DNA Sequence Determination by Hybridization:A Strategy for Efficient Large-Scale Sequencing," Science,260(5114):1649-1652, 1993.
Broude, N.E., et al., "Enhanced DNA Sequencing by Hybridization," PNAS, 91(8):3072-3076,1994.
Levene, M.J., et al., "Zero-Mode Wave guides for Single-Molecule Analysis at High Concentrations," Science, 299(5607):682-686,2003.
Fologea, D. et al., "Detecting Single Stranded DNA with a Solid State Nanopore," Nano Letter,5(10):1905-1909, 2005.
Meller, A., et al., Rapid Nanopore Discrimination Between Single Polynucleotide Molcules, PNAS,97(3):1079-1084,2000.
X. Huang and A. Madan, "CAP3: A DNA Sequence Assembly Program," Genome Research, 9(9): 868-877, 1999.
X. Huang et al., "PCAP: A Whole Genome Assembly Program," Genome Research, 13(9): 2164-2170,2003.
P.A. Pevzner et al., "An Eulerian Path Approach to DNA Fragment Assembly," PNAS,98(17):9748-9753,2001.
G. Sutton et al., "TIGR Assembler: A New Tool for Assembling Large Shotgun Sequencing Projects," Genome Science and Technology, 1(1}:9-19,1995.
E.W. Myers et al., "A Whole¬ Genome Assembly of *Drosophila*," Science, 287 (5461): 2196-2004,2000.
J.C. Venter et al., "The Sequence of the Human Genome," Science, 291 (5507):1304-1351,2001.
S. Batzoglou et al., "Arachne: A Whole-Genome Shotgun Assembler," Genome Research, 12(1):177-189,2002.
J. Sebat et al.,"Large-Scale Copy Number Polymorphism in the Human Genome," Science,305 (5683):525-528, 2004.
Z. Lai et al., "A Shotgun Sequence-Ready Optical Map of the Whole Plasmo diumfalciparum Genome," Nature Genetics,23(3):309-313,1999.
A Lim et al.,"Shotgun optical maps of the whole *Escherichia coli* 0157:H7 genome," Genome Research,11(9):1584-93, 2001.
West, J. et al., "Validation of S. pombe Sequence Assembly by Micro-array Hybridization," Journal of Computational Biology, 13(1): 1-20, Jan. 2006.
J. Jing et al., "Automated High Resolution Optical Mapping Using Arrayed, Fluid Fixated, DNA Molecules," Proc.Natl.Acad.Sci. USA,95:8046-8051,1998.
J. Lin etal. "Whole-Genome Shotgun Optical Mapping of Deinococcusradiodurans," Science, 285:1558-1562,Sep. 1999.
T. Anantharaman et al. "Genomics via Optical Mapping II: Ordered Restriction Maps," Journal of Computational Biology,4(2): 91-118,1997.
B. Mishra and L. Panda, "Partitioning Single-MoleculMaps into MultiplPopulations: Algorithms and Probabilistic Analysis," Discrete Applied Math, 104(1-3): 203-227, 2007.
International Hap Map Consortium,"The International Hap Map Project," Nature 426(18):789-796, 2003.
The International Hap Map Consortium, "A Haplotype Map of the Human Genome," Nature,437(27):1299-1320,2005.
M.Stephens and P.Donelly, "A Comparison of Bayesian Methods for Haplotype Reconstruction from Population Genotype Data," American Journal of Human Genetics,73(5):1162-1169,2003.
Kim, Sun et al., "Genome Sequencing Technology and Algorithms," Artech House, London, 2008, pp. 1-262.
Casey, Will et al., "Placing Probes Along the Genome Using Pairwise Distance Data," WABI 2001, LNCS 2149, pp. 52-66, 2001.
Mishra, Bud, "Comparing Genomes," Computing in Science and Engineering, pp. 42-49, Jan./Feb. 2002.
Aston, Christopher et al., "Optical Mapping and its Potential for Large-Scale . . . ," Elsevier Science, vol. 17, pp. 297-302, Jul. 1999.
Anantharaman, T.S. et al., "Fast and Cheap Genome Wide Haplotype Construction Via . . . ," WABI2001, pp. 1-14, Aug. 2001.

(56) References Cited

OTHER PUBLICATIONS

Anantharaman, Thomas et al., "False Positives in Genomic Map Assembly and Sequence Validation," WABI 2001, LNCS 2149, pp. 27-40, 2001.

* cited by examiner

210 — Algorithm 1: SUTTA – pseudo code

211 — Input: Set of $N$ reads
Output: Set of contigs

212 — $\mathcal{F} := \varnothing;$ /* Forset of D-trees */
213 — $C := \varnothing;$ /* Set of contigs */
214 — $\mathcal{B} := \cup_i^N \{r_i\};$ /* All the available reads */

215 —
```
while (B ≠ ∅) do
    r := B.getNextRead();
    If ( ¬isUsed(r) && ¬isContained(r) ) then
        DT := create_double_tree( r );
        F := F ∪ { DT };
        Contig CTG := create_contig( DT );
        C := C ∪ { CTG };
        CTG.layout();              /* Compute contig layout */
        B := B \ { CTG.reads };    /* Remove used reads */
    else
                                   /* jump to next available read */
    end
end
return C;
```

Algorithm 2: Node expansion

Input: Start read $r_0$, max queue size $\mathcal{K}$, percentage $\mathcal{T}$ of top ranking solutions
Output: Best scoring leaf 221    $\mathcal{T} := \emptyset;$            /* Set of leaves */
     $\mathcal{L} := \{(r_0, g(r_0))\};$   222    /* Live nodes (priority queue) */
     while ($\mathcal{L} \neq \emptyset$) do    223

224
```
    L := Prune(L, K, T);              /* Prune the queue */
    r_i := L.getNext();               /* Get the best scoring node */
    L := L \ {r_i};
    If (no reads align with r_i) then
        T := T ∪ {r_i};               /* ri is a leaf */
    else
        Add contained reads to r_i;
            /* Branch on r_i generating r_{i_1}, r_{i_2},....r_{i_M} */
        for (j=1 to M) do
            L := L ∪ {(r_{i_j}, g(r_{i_j}))};
        end
    end
end
return max r_j ∈ T {g(r_j)};
```

F I G. 2B

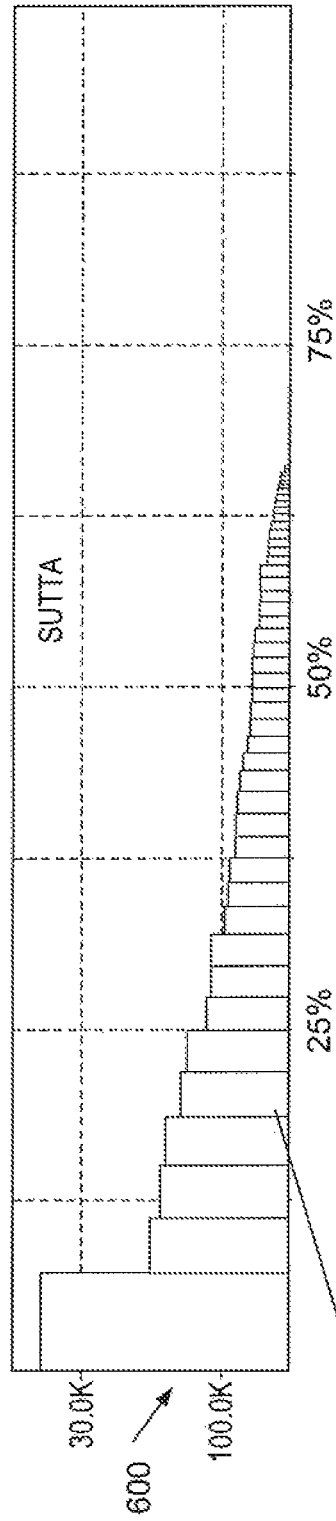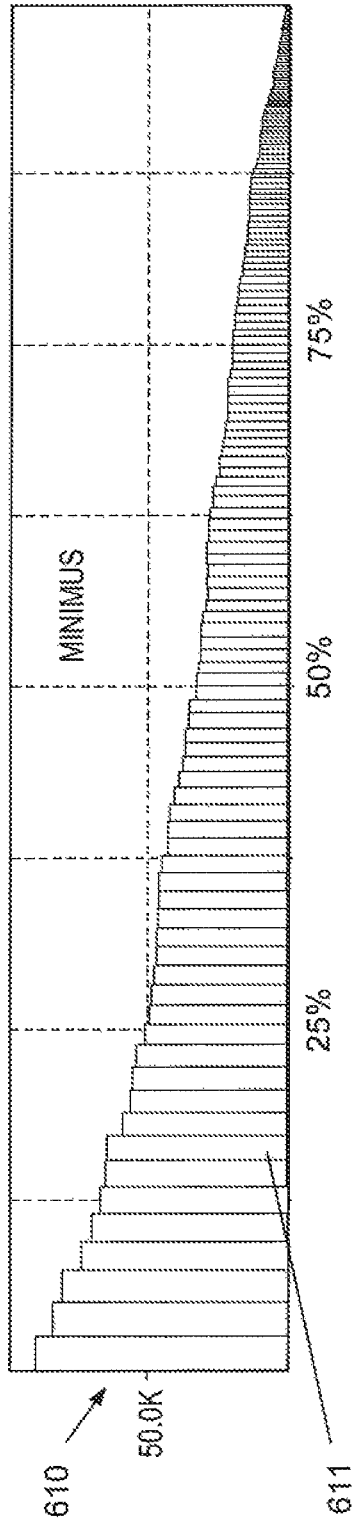
FIG. 6

| Genome | Assembler | # contigs | # big contigs (>10 kbp) | Max contig size (kbp) | Mean big contig size (kbp) | N50 (kbp) | Big contig coverage (%) |
|---|---|---|---|---|---|---|---|
| Brucella Suis | Minimus | 203 | 101 | 89 | 30 | 32 | 93.1 |
| | TIGR | 108 | 67 | 182 | 48 | 57 | 98.8 |
| | CAP3 | 1321 | 35 | 18 | 12 | 4 | 12.7 |
| | Phrap | 280 | 118 | 82 | 22 | 19 | 78.4 |
| | Phrap | 54 | 23 | 434 | 126 | 199 | 103.2 |
| | SUTTA[c] | 73 | 53 | 268 | 62 | 79 | 99.2 |
| | SUTTA[a] | 73 | 45 | 396 | 72 | 98 | 98.4 |
| Wolbachia Sp. | Minimus | 1545 | 37 | 16 | 13 | 2 | 40.7 |
| | TIGR | 1080 | 46 | 46 | 20 | 5 | 73.6 |
| | CAP3 | 1661 | 1 | 10 | 10 | 2 | 0.7 |
| | Phrap | 604 | 0 | 6 | 0 | 1 | 0 |
| | Phrap | 2253 | 55 | 64 | 22 | 1.8 | 98.5 |
| | SUTTA[c] | 1089 | 39 | 87 | 26 | 6 | 80.8 |
| | SUTTA[a] | 1068 | 27 | 181 | 39 | 6 | 83.5 |
| Staphylococcus Epidermidis | Minimus | 425 | 86 | 119 | 10 | 19 | 80.7 |
| | TIGR | 94 | 38 | 230 | 68 | 100 | 99.8 |
| | CAP3 | 1219 | 39 | 21 | 13 | 5 | 20.2 |
| | Phrap | 192 | 75 | 78 | 29 | 32 | 85.6 |
| | Phrap | 86 | 22 | 357 | 123 | 183 | 103.9 |
| | SUTTA[c] | 65 | 33 | 268 | 78 | 98 | 98.7 |
| | SUTTA[a] | 64 | 24 | 756 | 108 | 148 | 99.1 |
| Steptococcus Suis | Minimus | 1023 | 8 | 13 | 11 | 3 | 4.6 |
| | TIGR | 752 | 41 | 36 | 14 | 6 | 30.2 |
| | CAP3 | 534 | 43 | 36 | 15 | 7 | 32.8 |
| | Phrap | 408 | 43 | 36 | 15 | 7 | 32.8 |
| | Phrap | 485 | 53 | 36 | 15 | 9 | 41.9 |
| | SUTTA[c] | 503 | 48 | 36 | 15 | 8 | 37.5 |
| | SUTTA[a] | 510 | 46 | 48 | 17 | 8 | 39.8 |
| Steptococcus Uberis | Minimus | 644 | 28 | 26 | 13 | 5 | 19.8 |
| | TIGR | 563 | 56 | 30 | 15 | 8 | 46.3 |
| | CAP3 | 83 | 12 | 31 | 17 | 11 | 11.2 |
| | Phrap | 255 | 67 | 44 | 17 | 14 | 64.7 |
| | Phrap | 274 | 67 | 45 | 19 | 15 | 69.8 |
| | SUTTA[c] | 297 | 66 | 68 | 18 | 14 | 66.4 |
| | SUTTA[a] | 293 | 66 | 68 | 18 | 14 | 67.2 |

FIG. 8

METHOD, COMPUTER-ACCESSIBLE MEDIUM AND SYSTEMS FOR SCORE-DRIVEN WHOLE-GENOME SHOTGUN SEQUENCE ASSEMBLE

CROSS-REFERENCE TO RELATED APPLICATION(S)

The present application relates to and claims priority from International Patent Application No. PCT/US2009/069509 filed on Dec. 23, 2009, and from U.S. Patent Application Ser. No. 61/140,831 filed on Dec. 24, 2008, the entire disclosures of which are hereby incorporated herein by reference.

STATEMENT REGARDING FEDERALLY SPONSORED RESEARCH

The present disclosure was developed, at least in part, using Government support under Contract No. 1 R21HG003714-01 awarded by the NHGRI of National Institutes of Health. Therefore, the Federal Government may have certain rights in the invention.

FIELD OF THE DISCLOSURE

Exemplary embodiments of the present disclosure relate generally to methods, computer-accessible medium, and systems for assembling haplotypic and/or genotypic genome sequences. These exemplary sequences may be assembled from, e.g., short non-contextual sequence-read data, as may be obtained by various available and/or anticipated sequencing technologies, such as, e.g., 454, ABI-SOLID, Complete Genomics, Nanopore-based Sequencing, Pacific Biosciences, Sanger Sequencing, Sequencing-by-Synthesis, Sequencing-by-Ligation, Sequencing-by-Hybridization, Solexa, etc. Additional usage can also be sought from long-range low resolution contextual information, such as, e.g., mated pairs, single-molecule maps, reference sequences, base-composition, etc. Exemplary embodiments of the present disclosure also relate generally to use of whole and/or partial genomic and/or meta-genomic shotgun assembly, such as, e.g., in methods, computer-accessible medium, and systems for generating genome information, which may be obtained at any suitable pre-defined resolution, haplotypic ambiguity and/or accuracy (e.g., whole-genome physical mapping), or may be targeted at one or more selected regions of one individual genome, or a collection of genomes (e.g., ecological sample of many bacterial genomes or genomes of collection of cells in a polyclonal tumor), a class of technology that may be referred to as "long-range haplotypic sequence assembly." An exemplary procedure according to exemplary embodiments of the present disclosure may be referred to, e.g., as "Scoring-and-Unfolding Trimmed Tree Assembler" ("SUTTA").

BACKGROUND INFORMATION

Future Challenges of Sequencing Biotechnology: Currently, there appears to be a need for a relatively inexpensively priced (e.g., less than $1,000 and/or $800-$1,200) genome sequencing technology of acceptable accuracy (e.g., on the average, one base error in less than 10,000 bps and/or one base error in 8,000 bps-12,000 bps) and high-speed (e.g., complete processing time for sequencing of less than one day, and/or twelve to thirty-six hours). There may also be a need to incorporate in the technology the capability to be continuously improved upon and/or afford many simultaneous and/or successive increasingly and/or exponentially rapid improvements over the near and/or long-term (e.g., one month, six months, one year, five years, ten years, twenty-five years, fifty years, one-hundred years, etc.). To incorporate such features, the technology should have the capability to handle single molecules, work with a few and/or even single cells, operate at a nano-scale resolution and a femto-second speed, and be agnostic and/or independent to some, most and/or all of the available and anticipated short-sequence-read technologies. Thus, the technology should anticipate the needs to work with a minute amount of material, avoid amplification, be non-invasive, asynchronous and non-realtime. It should consider and/or integrate, e.g., ideas, methodologies and/or implementations from multiple disciplines with appropriate abstractions, modularity and hierarchy. For example, the technology should aim for optimal integration of multiple technologies, such as, computational, physical, and chemical, with more emphasis on the technologies enumerated earlier in this order. In addition, the integrated technology should be error resilient, achieving relatively high reliability outcomes from relatively low reliability source(s), and intelligently selecting parameters modulating various 0-1 laws that shape and influence the quality of the experimental outcomes.

If it was possible to be reasonably assured of the correctness/accuracy of the assembly of the reference genotype sequence, that the polymorphisms are relatively rare and uniformly distributed, and that the population genetics has very few admixtures of separate ancestries, it could suffice to merely generate massive amounts of short reads that could be aligned to a reference sequence, thus enabling a relatively simple technology to study any individual's genomic make-up. In the absence of a genuine confidence in these underlying assumptions, however, there appears to be a need for technologies that can be coupled to, e.g., computational algorithms, etc., to assemble whole genome haplotypic sequences with an acceptable level of accuracy. Developing technologies combining optical mapping, hybridization data obtained with PNA/LNA probes and procedures to solve local positional sequencing-by-hybridization (PSBH) problem indicates one possible approach to this problem. However, the algorithms at the core of this SBH technology appear to be incapable of exploiting many other advances in sequencing technologies that focus only on producing non-contextual short-sequence-read data.

In contrast, as described below, exemplary embodiments of the present disclosure can utilize and/or emphasize the power of Bayesian procedures in combining short-range high-accuracy sequence reads with long-rage low-resolution information in order to assemble the reads to produce acceptably accurate haplotypic whole-genome sequences. Currently available technologies do not achieve the objectives of a scalable whole-genome haplotypic sequencer. For example, such conventional technologies generally generate relatively short genotypic reads (e.g., 30 bps-300 bps, without haplotypic and locational context); they generally are corrupted by errors, such as low-quality base-calls or compression of homopolymeric runs; and they frequently lack long-range contextual information (except what may be available through a limited amount of mate-pair data). These shortcomings in the currently available technologies generally affect the yield and speed of the resulting technology and can have a debilitating effect on the complexity of the assembly procedure.

Possible Need to Meet Such Challenge (e.g., to facilitate sequencing): To meet the challenges of long-range haplotypic sequencing, there should be a technology design principle that does not just focus on base-by-base reads, but also takes into account the tractability of the procedures that should be needed to handle the resulting data. Otherwise, the cost improvement and throughput gain at the single-base level could be squandered at the whole-genome level. Sequencing technologies are usually thought of in terms of the two extremes: at one extreme are technologies such as Sanger sequencing, which works by producing a correct index for every base, but extends over a short range; at the other extreme are technologies such as nanopore-based sequencers that aim for (potentially) long reads, but generally lack location information. There is a large design space between these two extremes, in which the trade-offs between read-sizes and accuracy in locational information can be explored and/or evaluated.

A relatively simple, cost effective, flexible and evolvable solution to the dilemma posed by the current situation, where it is possible to generate successively superior non-contextual base-reads, but failing to assemble these reads to create a global view, can be to target the core shotgun assembly procedures for significant improvements. While it may first appear that such an approach would entail an unacceptably large increase in the computational cost or loss of accuracy, as described below, exemplary embodiments of the present disclosure demonstrate that these two aspects of the problem may not pose a significant problem for realistic datasets and can also be further improved through judiciously chosen long-range information that may be collected separately and in parallel.

Related Technologies: Sequencing, Mapping and Haplotyping: Recent advances in genomic sciences have created new opportunities for identifying many of the genes commonly implicated in diseases, and elucidating many of the cellular pathways upon which they act. Ultimately, these advances are expected to pave the way for a new science of individualized medicine, where the population based association studies would lead to immediately customize and target therapies for specific diseases in specific individuals, for example. The underlying advances have generally come from three independent sources: (1) New Generation Sequencing (NGS) Technologies that can generate a massive amount of short reads covering a whole genome many times, (2) Ultra-High-Coverage Single Molecule Mapping (SMM) Technologies (e.g., Optical Mapping or AFM Mapping) that can provide whole-genome-wide long-range contextual information, and (3) Large-scale Population-wide polymorphism studies of Structural Variations (SVs) among genomes. These component technologies will be described first, while pointing out that the polymorphism-study technology (e.g., ArrayCGH or clone sequencing) still remains in its infancy stages.

Recently, there have appeared many new ideas and approaches for generating short sequence reads from genomes relatively quickly, cheaply and in massive amount. For example, the classical dideoxynucleotide termination DNA sequencing technology, introduced by Fred Sanger in 1977 and commonly known as "Sanger Sequencing" technology, had been routinely used for large-scale sequencing at least until very recently, e.g. Smith, L. M. et al. "Fluorescence Detection in Automated DNA Sequence Analysis," Nature, 321(6071); 674-679, 1986. Over the years, the technology has been streamlined with better latency and higher throughput through improved, parallel and rapid sorting of fragments using capillary gel electrophoresis, thus addressing some of the inherent limitations posed by Joule-heating during fragment separation using slab gels, for example. Despite these improvements, however, two predominant limitations have remained with such prior technology: the read-lengths cannot exceed about one Kb, and the reads have no associated contextual information (e.g., no chromosomal location or haplotypic disambiguation). Several new massively parallel sequencing methods have been proposed to address many of these issues; but, while most of these methods have provided lower latency and higher throughput at a lower cost, they have neither improved the read lengths nor enabled addition of contextual information. For example, few representatives of these new classes of massively parallel short-read sequencing technologies are "Sequencing by Synthesis Pyrosequencing," e.g., Nyren, P. et al., "Solid Phase DNA Minisequencing by an Enzymatic Luminometric Inorganic Pyrophosphate Detection Assay," Annal Biochem 208(1): 171-175, 1993; Ronaghi, M. et al., "PCR-Introduced Loop Structure as Primer in DNA sequencing," Biotechniques, 25(5): 876-884, 1998; Margulies, M. et al., "Genome Sequencing in Microfabricated High-Density Picoliter Reactors," Nature, 437(7057): 376-380, 2005. However, another technology, e.g., Pacific Biosciences' stated goal is to create a technology that can read up to 5-75 Kb without increasing the cost. While such advancements should have a positive effect on various exemplary embodiments of the present disclosure, Pacific Biosciences' technology, in isolation, generally provides only limited improvement over other related technologies, as it lacks long-range information (e.g., information spanning over genomic regions of size 150 Kb or greater, or 100 Kb or greater).

Pyrosequencing is a sequencing-by-synthesis technology. In pyrosequencing, upon nucleotide incorporation by the polymerase, the released pyrophosphate is converted to ATP by action of the enzyme sulfurylase, with necessary energy source to convert luciferin to oxyluciferin and light. Because in sequencing by synthesis, during each cycle a single nucleotide species (e.g., A, T, C or G) is used for querying, detection of the emitted light in each reaction cycle provides the information as to which particular base (and possibly how many) was incorporated in that reaction cycle. By combining the information from many successive cycles it is possible to read a large number of sequences in parallel. These sequencing technologies have found many applications: e.g., SAGE profiling, cDNA sequencing, nucleasome positioning and metagenomics, but do not seem to be appropriate or cost-effective for population genomics, personal genomics or genomics-based individualized medicine, for example.

One embodiment of pyrosequencing occurs in the 454 GS-20 sequencing instruments, e.g., Margulies, M. et al., "Genome Sequencing in Microfabricated High-Density Picolitre Reactors," Nature, 437(7057): 376-380, 2005. This instrument integrates and parallelizes the entire process—starting from library construction to sequence detection. For example, starting with a genomic library of 500 bp-long fragments, the ends of fragments are first repaired, then ligated with 454-specific linkers, and finally, coupled to Sepharose beads with covalently linked complementary oligoes that can hybridize to the fragment library's ligated linkers. The bead/DNA complexes are emulsified in oil suspension containing aqueous PCR reagents in order for PCR amplifications to occur for each library-fragment producing many identical PCR products, all attached to the same bead; pyrosequencing reactions can then be carried out on these PCR products simultaneously as long as sequence detections can be achieved reliably and synchronously. The pyrosequencing reactions are carried out on the beads, once they are suitably arrayed on a Pico Titer Plate (PTP) device with sensors (fused optical fibers) engineered on to them. At the end of the process, software is used to deconvolve the optical data into about 400,000 sequencing reads of 250 bp reads (about 100 Mb in total) over 7 hours. However, the read-length is relatively short (only 250 bp) and the 400,000 fragments have no contextual information. In addition, since, in each cycle, there is no unambiguous way of determining exactly how many bases get incorporated, if the genomic fragment has a run of a single nucleotide base, 454-instrument will not be able to tell the run length, and thus produce a compression of the homopolymeric run to a single base.

In order to circumvent the problem of compression of homopolymeric runs, it is possible to employ a more complex reversible dye-terminator chemistry, as in the platform built by Solexa, Ltd., for example. Starting with a library of genomic fragments, which are then linker ligated, they are amplified in situ following hybridization to complementary oligoes, covalently linked to a flow cell surface. The fragments are then amplified into clusters of PCR products, denatured, annealed with sequencing primers, and then read by a sequencing-by-synthesis approach to detect the 3'-blocked fluorescent-labeled nucleotide incorporated in a reaction cycle. Using this approach, a Solexa instrument currently reads about 60 million sequences, each of read-length no larger than 50 bp. Similar to the other technologies, the read-lengths from this technology are even shorter and may have little or no contextual problem; despite being able to read almost 1× coverage of a genotypic human genome in a single run, these reads fail to assemble to give any meaningful information. Even in simple resequencing applications, lack of contextual information poses serious difficulties in placing the short sequence reads in the reference sequence efficiently and correctly.

In addition to these technologies, there are other technologies, such as, ligation-based sequencing (building on genotyping methods used in ligation-chain-reaction (LCR) and oligonucleotide ligation assay (OLA)), sequencing by hybridization (a variant called SMASH (Single Molecule Approach to Sequencing by Hybridization) replaces array-based hybridization with hybridization to single molecules that are then queried on a surface), sequencing with zero-mode waveguide and nanopore sequencing approaches. Further discussions of these topics can be found in the literature, e.g. Barany, F., "The Ligase Chain Reaction in a PCR World," *PCR Methods Appl.*, 1(1): 5-16, 1991; Nickerson, D. A., et al., "Automated DNA Diagnostics Using an ELISA-Based Oligonucleotide Ligation Assay," *PNAS*, 87(22); 8923-8927, 1991; Drmanac, R., et al., "DNA Sequence Determination by Hybridization: A Strategy for Efficient Large-Scale Sequencing," *Science*, 260(5114): 1649-1652, 1993; Broude, N. E., et al., "Enhanced DNA Sequencing by Hybridization," PNAS, 91(8):3072-3076, 1994; Levene, M. J., et al., "Zero-Mode Waveguides for Single-Molecule Analysis at High Concentrations," *Science*, 299(5607): 682-686, 2003; Fologea, D. et al., "Detecting Single Stranded DNA with a Solid State Nanopore," *Nano Letter,* 5(10):1905-1909, 2005; and Meller, A., et al., "Rapid Nanopore Discrimination Between Single Polynucleotide Molcules, *PNAS,* 97(3): 1079-1084, 2000.

However, a massively large number of such non-contextual short-reads can only lend themselves to biological interpretations and biomedical applications when they can be assembled into contiguous overlapping sequences encompassing the information contained in each haploid chromosome. Given the limitations of the current biotechnology instruments, such interpretations have to be obtained indirectly through computational algorithms. The resulting classes of algorithms have come to be known as "shotgun assembler," and have aimed only to provide draft-quality (1 bp error on the average in 10 Kb) accuracy genotype sequence contigs that cover repeat-free regions in the genomes, and that align and phase with respect to a scaffold, but that remain oblivious to rearrangement/translocation and orientation/inversion error. Even though researchers have significantly improved the ability to create a large-coverage library of sequence reads relatively quickly and cheaply, counterintuitively, the resulting technology has not increased the value of the information, thus obtained. It is because most of these technologies produce shorter read-lengths, corrupt the data with different forms of base-read errors, and are not amenable to assembly processes that would provide useful long-range information, for example.

There are large numbers of shotgun assembly algorithms that differ from each other in a subtle way, but roughly follow a general set of strategies. In general, it is not difficult to see that if, hypothetically, the genomes could be idealized as completely random sequences, the assembly problem could be easily solved with a simple and efficient (e.g., with a polynomial expected time-complexity) algorithm that would use the significant overlaps among the sequence reads to create an overlay and then determine a consensus sequence by combining the bases that align positionally. On the other hand, for example, if the computed genome sequence is desired to be the most parsimonious solution (e.g., the shortest) among all possible sequences containing all of the sequence reads, then it should suffice to compute the shortest common super-sequence of the sequence-reads, which, however, would require solving an NP-hard problem. The dilemma can be solved by first computing a greedy solution by successively combining the inter-sequence-read-overlaps in a reasonably good order (e.g., always selecting the most significant overlap among all the unused overlaps) and then heuristically correcting regions of the overlay in some plausible manner, whenever possible; regions that do not yield to these error-correction heuristics are abandoned as irrecoverable and shown as gaps. In this manner, these greedy algorithms may trade computational complexity against loss of genotypic information, number of gaps separating contigs and accuracy of the assembly. As described below, exemplary embodiments of the present disclosure, in contrast, can promote an approach that could potentially lead to an exhaustive search over all possible overlays, but still tames the computational complexity through a constrained search as it identifies implausible overlays quickly through a score-function. Such a score function can be, for example, based on, e.g., statistical properties of the sequencing technology, errors in the sequence reads and genome structure, or based on side-information provided by the long-range mapping information.

The classical greedy shotgun assembly algorithms use a general procedure that include the following substeps: (1) Fragment readout: The sequence-reads from each fragment are determined by an automatic base-calling software (exemplary embodiments of the present disclosure can use the standard software in a pre-processing step); (2) Trimming vector sequences: Part of the vector sequences that could have been included during the sequence read phase are removed (exemplary embodiments of the present disclosure can use the standard software in a pre-processing step); (3) Trimming low-quality sequence: Often the raw sequence reads contain low-quality base-calls, which confuse the estimation of the overlap significance, and introduce insurmountable difficulties for the greedy shotgun assembly algorithms. The greedy shotgun assembly algorithms usually remove or mask the low-quality base-calls in order to improve the accuracy of their sequence assembly (exemplary embodiments of the present disclosure may not need to use this software as it may incorporate the quality values in its over-all score function to eliminate false-positive overlaps); (4) Fragment assembly: The shotgun sequence reads are used greedily to generate an overlay of aligned fragments to create contigs; (5) Fragment validation: Correctness of each assembled contig is assessed either manually or by certain extraneous heuristics (exemplary embodiments of the present disclosure may not require such a step as the validation is implicit in its tree-pruning algorithm); (6) Scaffolding contigs: The computed contigs are oriented, phased and ordered. Currently, the greedy shotgun assembly algorithms use the limited size/distance information that can be inferred from mate-pair data, prepared by reading both ends of clones; (7) Finishing: The gaps between adjacent contig pairs, together with their locations and sizes, are inferred by the scaffolding step, and these gaps are closed by targeted sequencing. For additional references, see Kim, S. et al., *Genome Sequencing Technology and Algorithms*, Artech House, London, 2008.

One of the important sub-steps in the general procedure described above can be the fourth step, e.g., the one labeled "Fragment Assembly." The greedy shotgun-assembly algorithms generally employ the overlap-layout-consensus approach, consisting of three major steps: (a) identification of candidate overlaps, (b) fragment layout, and (3) consensus sequence generation from the layout. The first step is achieved by a string pattern matching technique, which generates possible overlaps between fragments. The second step, as implemented in currently available shotgun assemblers, are usually greedy, but vary in subtle ways from implementation to implementation, namely, the simplest implementations are often based on a very simple greedy approach that examines one overlap after another; the most sophisticated ones use some graph-based direct representation of the overlaps or indirect ones using k-mers in the sequence-reads that encode the maximal overlaps (in a De Bruijn graph representation), followed by a greedy search of the graph after some initial pruning. Certain complications occur as one needs to deal with sequence-read-pairs that contain one in the other, chimeric sequence reads, sequences that may contain low-quality base-calls or regions of vector sequences, or sequence reads originating from repetitive regions.

For example, in CAP3 sequence assembler, the overlaps are determined by an optimal local alignment algorithm and then evaluated with respect to five measures: minimum length, minimum percent identity, minimum similarity score, differences between overlapped reads at high-quality base-calls, and differences between the rate of error at the overlaps under consideration, relative to a global sequencing error estimates. See, e.g., X. Huang and A. Madan, "CAP3: A DNA Sequence Assembly Program," *Genome Research*, 9(9): 868-877, 1999; X. Huang et al., "PCAP: A Whole Genome Assembly Program," *Genome Research*, 13(9): 2164-2170, 2003. In CAP3, an initial layout of reads is created by a greedy method using overlap scores in decreasing order. Assuming mate-pair information is available, the quality of the current layout is assessed by the paired reads and the inferred distances between them. Consequently, regions of a layout with large number (using an extremal statistics) of unsatisfied mate-pair-constraints can be identified, and input to an algorithm that aligns unaligned pairs according to their distances, and attempts to correct these regions by adding satisfiable mate-pairs and "breaking" unsatisfiable pairs, repetitively, as long as progress can be made. Finally, contigs are ordered and linked with unsatisfied constraints, where corresponding mate-pairs link paired sequences in two adjacent contigs. Similar ideas also occur in TIGR and PHRAP assemblers: e.g., P. Green, http://www.phrap.org; G. Sutton et al., "TIGR Assembler: A New Tool for Assembling Large Shotgun Sequencing Projects," *Genome Science and Technology*, 1(1): 9-19, 1995; J. D. Kececioglu, and E. W. Myers, "Combinatorial Algorithms for DNA Sequence Assembly," *Algorithmica*, 13(1-2): 7-51, 1995;

As an example of a graph-based approach, it is possible to consider the Celera Whole Genome Assembler (WGA), which has been used to genotypically assemble WGS sequence-reads of many large eukaryotic genomes. See, e.g., E. W. Myers et al., "A Whole-Genome Assembly of *Drosophila*," *Science*, 287(5461): 2196-2004, 2000; J. C. Venter et al., "The Sequence of the Human Genome," *Science*, 291 (5507): 1304-1351, 2001; Celera WGA first constructs a graph of approximate overlaps between every pair of WGS sequence-reads, followed by a step to partition the graph by assigning an orientation to each fragment (forward or reverse complement) through a branch-and-bound search (in contrast to exemplary embodiments discussed herein below, Celera's branch-and-bound procedure is used to solve a simpler subproblem), and terminated by selecting a set of overlaps that induces a consistent layout of oriented sequence-reads and merging the resulting multiple sequence alignments into a consensus sequence. Celera WGA's algorithm can only be employed to search for solutions of a relatively simpler subproblem of orientation assignment, while exemplary embodiments of the present disclosure can use branch-and-bound approach to search the space of all possible layouts that yield the correct orientations as a byproduct. Importantly, their score function is based on the overlap scores of pairs in two possible relative orientations (same or opposite orientation), and neither includes any non-local statistics or long-range information, nor can it be extended in any meaningful way to incorporate such information as it lacks structures of genomic subpaths. Consequently, unlike various exemplary embodiments of the present disclosure, Celera WGA's branch-and-bound approach does not provide a significant performance improvement in practice, and forces them to adapt the implementations to a hybrid approach that mixes branch-and-bound steps with greedy steps, in direct contrast to some exemplary embodiments in accordance with the present disclosure.

For other instantiations of graph-based greedy approach to shotgun sequence assembly, it is possible to consider the Arachne and EULER assemblers. See, e.g., S. Batzoglou et al., "Arachne: A Whole-Genome Shotgun Assembler," *Genome Research*, 12(1): 177-189, 2002, P. A. Pevzner et al., "An Eulerian Path Approach to DNA Fragment Assembly," *PNAS*, 98(17): 9748-9753, 2001. Like Celera WGA assembler, Arachne has also found applications in large-scale genome assembly projects, but suffers from various problematic features discussed earlier (e.g., potential misassembly of rearrangements, haplotypic ambiguities, etc.). Arachne proceeds through several steps: (a) Overlap detection and alignment: computed by identification of k-mers of length 24, merging of shared k-mers, extension of shared k-mers to alignment and a refinement to optimal alignment by dynamic programming, (b) Error correction (using a majority rule heuristics), (c) Alignment evaluation (by a penalty score that penalizes base-call discrepancies), (d)

Identification of mate pairs (by successively combining two overlapping pairs and repeating an augmentation step), (e) Contig Assembly (by merging and extending sequence-reads until putative repeat boundaries are encountered), (f) Detection of repeat contigs, (g) Scaffold Generation with supercontigs, and (h) finally, Gap filling in supercontigs.

EULER assembler sidesteps direct use of "overlap-layout-consensus" approach, by creating a De Bruijn graphs out of (k–1)-suffixes and prefixes of k-mers, and by searching for Eulerian superpaths in the resulting De Bruijn graphs after some initial pruning. Thus it incorporates several heuristics to disentangle clusters of erroneous edges, which may confuse the algorithm to explore incorrect superpaths and getting it stuck with incorrect solution, especially when the quality of base-calls falls below a certain threshold. EULER tries to circumvent these problems by an error-correction process, which is not always foolproof. In addition, it also attempts to improve the accuracy of the algorithm by a series of graph-transformation heuristics that coalesce or partition collections of superpaths. In certain variations (e.g., EULER-DB and EULER-SF), this algorithm has been modified to exploit the information available through mate-pairs (e.g., by creating artificial paths or scaffolds, respectively). However, none of these algorithms use long-range information to, e.g., score solutions, and are generally not flexible enough to adapt to other long-range data. They also do not, e.g., seek to avoid rearrangement errors or haplotypic ambiguities.

Certain recent advances in the genomic sciences have aimed to compensate for the deficiencies of the short-range sequencing technologies, and have primarily come from mapping technologies that can include, e.g., optical mapping and array-mapping techniques, and enable a broad and long-range view of the whole genomes. In addition they have played a significant role in validating sequence assemblies that are prone to massive amount of otherwise undetectable errors. Such techniques are described, e.g., in Z. Lai. et al., "A Shotgun Sequence-Ready Optical Map of the Whole *Plasmodium falciparum* Genome," *Nature Genetics*, 23(3): 309-313, 1999; A Lim et al., "Shotgun optical maps of the whole *Escherichia coli* O157:H7 genome," *Genome Research*, 11(9): 1584-93, September 2001; W. Casey, B. Mishra and M. Wigler, "Placing Probes along the Genome using Pair-wise Distance Data," *Algorithms in Bioinformatics*, First International Workshop, WABI 2001 Proceedings, LNCS 2149:52-68, Springer-Verlag, 2001; B. Mishra, "Comparing Genomes," Special issue on "Biocomputation:" *Computing in Science and Engineering.*, pp 42-49, January/February 2002; J. West, J. Healy, M. Wigler, W. Casey, and B. Mishra, "Validation of *S. pombe* Sequence Assembly by Micro-array Hybridization," *Journal of Computational Biology*, 13(1): 1-20, January 2006; C. Aston, B. Mishra and D. C. Schwartz, "Optical Mapping and Its Potential for Large-Scale Sequencing Projects," *Trends in Biotechnology*, 17:297-302, 1999.

To some degree, it is possible to argue that the paper of Aston-Mishra-Schwartz had recognized how in principle long-range information from optical maps could assist shotgun sequence assemblers in assembly, contig-phasing and error-correction. However, the key assumptions of that paper, namely, optical map assembly algorithms can be presumed to scale to any genome size in the presence of any error process (e.g., optical chimerism), has not proven to hold in reality. Granted that at intermediate scale (e.g., bacteria sized genomes) optical mapping has been phenomenally successful in cost, throughput and accuracy, and that Aston-Mishra-Schwartz strategies have worked reasonably well in those cases, myriads of problems arise as one attempts to apply the same strategies to eukaryote-sized genomes, or desire to distinguish haplotypes. For instance, there is still no eukaryotic example (e.g., human or plant) where whole-genome optical-map-assisted high-quality haplotypic sequence assembly has been achieved. However, as described below, exemplary embodiments of the present disclosure can provide insight and remedies for overcoming the shortcomings of the Aston-Mishra-Schwartz strategy, for example.

During an approximately decade-long effort directed at optical mapping, single molecule optical mapping technology was developed for clones in 1998 (see, e.g., J. Jing et al., "Automated High Resolution Optical Mapping Using Arrayed, Fluid Fixated, DNA Molecules," *Proc. Natl. Acad. Sci. USA*, 95:8046-8051, 1998) and for whole microbial genomes in 1999 (see, e.g., J. Lin et al. "Whole-Genome Shotgun Optical Mapping of *Deinococcus radiodurans*," *Science*, 285:1558-1562, September 1999). In particular, a genome wide ordered restriction map of a single nucleic acid molecule, e.g., double stranded DNA, may be generated using optical mapping techniques, e.g., fluorescent microscopy (see, e.g., J. Jing et al., "Automated High Resolution Optical Mapping Using Arrayed, Fluid Fixated, DNA Molecules," *Proc. Natl. Acad. Sci. USA*, 95:8046-8051, 1998).

A person having an ordinary level of skill in the art should understand how to generate a genome wide restriction map. Briefly, uncloned DNA (e.g., DNA directly extracted from cells after lysis) may be randomly sheared into approximately 0.1-2 Mb pieces and attached to a charged glass substrate, where the DNA may be cleaved with a restriction enzyme, then stained with a dye (e.g., a fluorescent dye). The restriction enzyme cleavage sites appear as breakages in the DNA under e.g., a fluorescent microscope. Using predefined techniques, the optical mapping of breakages produces a genome wide restriction map.

Exemplary procedures can be used to generate genome wide genotype or haplotype maps from optical mapping data (e.g., optical mapping probe data and/or optical mapping restriction data) may be based on Bayesian/Maximum-Likelihood estimation as described, e.g., in T. Anantharaman et al. "A Probabilistic Analysis of False Positives in Optical Map Alignment and Validation," *WABI*2001, August 2001; and in T. Anantharaman et al. "Genomics via Optical Mapping III: Contiging Genomic DNA and variations," *ISMB*99, August 1999. More recent exemplary procedures for generating haplotype maps from optical mapping data may extend the older procedures to handle a mixture hypothesis of pairs of maps for each chromosome, corresponding to the correct ordered restriction maps of the two parental chromosomes. Such exemplary procedure is described, e.g., in T. Anantharaman et al. "Fast and Cheap Genome wide Haplotype Construction via Optical Mapping," *Proceedings of PSB*, 2005. In addition, International Publication No. WO 2008/112754, Mishra et al., September 2008, the entire disclosure of which is hereby incorporated by reference herein, relates generally to methods, computer-accessible medium, and systems for generating genome wide probe maps, as well as use of genome wide probe maps, e.g., in methods, computer-accessible medium, and systems for generating genome wide haplotype sequences that may be read at a pre-defined level of accuracy, for example.

Statistical modeling of the errors may be straightforward. However, a combinatorial version of the problem for finding a best map assembly may be theoretically computationally infeasible, e.g., it may be NP-hard and there may be no corresponding polynomial-time approximation scheme (PTAS). This theoretical high complexity may apply to both genotype and haplotype map assembly cases as well as to other related variants as described, e.g., in T. Anantharaman et al. "Genomics via Optical Mapping II: Ordered Restriction Maps," *Journal of Computational Biology*, 4(2): 91-118, 1997; and in B. Mishra and L. Parida, "Partitioning Single-Molecule Maps into Multiple Populations: Algorithms And Probabilistic Analysis," *Discrete Applied Mathematics*, 104(1-3): 203-227, August, 2000.

Such combinatorial results may suggest that any procedure used to find the best map assembly can utilize computational time that is super-polynomial (e.g., exponential) with respect to the size of the input data (under a widely-accepted hypothesis that P≠NP). However, by appropriate design of an experimental set-up, it has been demonstrated that one can constrain the problem to only polynomially feasible instances of a normally infeasible problem, as described, e.g., in T. Anantharaman et al. "A Probabilistic Analysis of False Positives in Optical Map Alignment and Validation," *WABI*2001, August 2001.

For example, it is possible to partition the sets of possible input data into two groups: an "easy" group having sufficiently low error rates or sufficiently high data coverage to compensate for the error rates, where probabilistic polynomial time solutions to the problem are possible; and a "hard" group for which no polynomial time solution may be known. Further, it may be relatively easy to classify a data set based on the amount of data and the error rates of the data as described, e.g., in T. Anantharaman et al. "A Probabilistic Analysis of False Positives in Optical Map Alignment and Validation," *WABI*2001, August 2001. The exemplary transition between the two data types of data sets may be quite sharp, which may result in a "0-1" law for useable data. This insight and its prudent exploitation has been useful in using optical mapping techniques to reliably generate a genome wide haplotype map, and it may be useful in providing suitable long-range information needed to scale sequence assembly algorithms to handle construction of haplotypic genome sequences, for example.

Although optical mapping methods may have been used to construct genome wide ordered restriction maps of whole genomes, such methods have not been used to assist genome-wide shotgun assembly of short sequence reads from any independent sequencing technologies in order to generate haplotype sequences. Accordingly, at least one of the objects of exemplary embodiments of the present disclosure is to facilitate and/or provide such procedure.

There also have been attempts to directly combine optical mapping with sequencing by in situ sequencing of immobile restriction fragments via nick translation. See, e.g., U.S. Pat. No. 6,221,592 entitled "Computer-based methods and systems for sequencing of individual nucleic acid molecules" to Schwartz, David C. and Mishra, Bhubaneswar. However, the problem of assembling such short sequence reads anchored to the restriction fragments can rely on exploiting the implicit locational information in the data and thus can require first explicitly creating an ordered restriction optical map and then interpreting the short reads (thus positionally anchored) appropriately via a technology-specific Bayesian prior model, for example. However, this approach may not cure certain problems because compression of homopolymeric can run as well as optical chimerism. Accordingly, at least one of the objects of exemplary embodiments of the present disclosure is to provide such procedure, while avoiding the problems of hompolymeric run compression and optical chimerism.

Exemplary embodiments of the present disclosure can also provide a direct method for individual (personal) haplotype sequencing, and can have significant implications to a study of a population and in characterizing important polymorphisms. With the stated successful completion of the human genome project (HGP), it has been generally assumed that with access to a reference human genome sequence, it would be easier to catalog individual genomic differences relative to the reference genome sequence and that the remaining challenges will only be in terms of designing (a) inexpensive experimental setups targeting relatively few and manageably small regions of polymorphic sites (e.g., about 30,000 haplotype blocks each encompassing no more than about 10 haplotypes), and (b) efficient algorithmic solutions for interpreting massive amount of population-wide polymorphism data. However, several implicit assumptions and hitherto unknown facts appear to impede progress along this direction.

For example, (i) currently available reference genome sequences tend to primarily provide genotypic information and remain to be validated as to their suitability in representing humans in a universal manner, (ii) all possible categories of dominant polymorphisms and their distributions have not been satisfactorily cataloged, (iii) haplotype data from a population can only be collected in many non-contextual short-range fragments that provide no meaningful long-range structural information, and (iv) such short-range data have to be phased statistically from population-wide distributions and with an inferred (assumed) distributions of recombination sites, which may differ significantly from the reality, etc. Exacerbating these fundamental hurdles, one also faces the added difficulty of dealing with highly intractable computational problems, which can arise from the requirement to interpret non-contextual short-range data from many individuals and many subpopulations (with unknown population stratification) relative to any genotypic reference sequence. As described in more detail below, the exemplary embodiments of the present disclosure can circumvent these difficulties by focusing on every individual in a population one at a time and by reconstructing their haplotypic genome sequences accurately without any reference to any other genome sequence(s) from another and/or many other individual(s) from the population.

If a competing non-contextual short-range sequence read technology is used, the sequence reads to the reference genome should be mapped using a relatively efficient and accurate sequence alignment algorithm, under the assumption that reads will contain small local polymorphisms and are nearly identical to their corresponding sequence in the reference genome. In practice, a low-coverage (e.g., 2 or 3×) sequencing project may be used to generate sufficient number of reads to characterize a very large number of positional variations on the target genome, for example. The entire approach may rest on the simplifying assumption that although the new generation sequencing technologies may be unsuitable for de novo genome sequencing, they may be adapted to genome resequencing. However, in this assumption, it remains unclear as to how one expects haplotypic ambiguities and structural variations to be handled satisfactorily.

For example, in studies based on a resequencing approach, it is assumed that it is of no significance to ignore most of the different sequence variations that individual carries and it suffices to concentrate the efforts on important common variations (e.g., ones carried by a large fraction of individuals in a population), as only these are likely to be disease associated. Following this reasoning, it is possible to first characterize all frequent genetic variations by short-range resequencing of a limited number of randomly selected individual from populations and using this information from genome-wide genotyping to determine allelic types for any previously characterized variation sites in the target genomes. For example, this approach has been the key component of the HapMap Project, which focuses only on mapping all common single nucleotide polymorphisms (SNPs). See, e.g., The International HapMap Consortium, "The International HapMap Project," *Nature* 426(18): 789-796, 2003; The International HapMap Consortium, "A Haplotype Map of the Human Genome," *Nature,* 437(27):1299-1320, 2005.

The HapMap project has been implemented in two phases: first, using the genomes of 269 individuals from different populations about a million SNPs were mapped across the genome, and later augmented with an additional 4.6 millions SNPs. Using population-wide correlations among the SNPs the sequences of SNP sites on the reference genomes were segmented into a small number of combination of alleles, with the consecutive segments assumed to be separated by recombination hotspots: the combinations are referred to as haplotypes and the segments as haplotype block. See, e.g., M. Stephens and P. Donelly, "A Comparison of Bayesian Methods for Haplotype Reconstruction from Population Genotype Data," *American Journal of Human Genetics,* 73(5): 1162-1169, 2003. The subsequent analyses on the population are carried out using these inferred blocks, independent of any validity as to whether the individual actually physically carries such haplotypes in its genome. Furthermore, a problematic circularity is inserted into the reasoning in this process as population, which is used for haplotype inference, is then analyzed by the same haplotypes to understand population stratification, disease association, and selection processes acting on these genomes.

With these traditional technologies, even more troublesome is the assumption that all sequence variations in the human genome are single nucleotide mutations, which has been seriously questioned by the rather serendipitous detection of copy-number polymorphisms through array-CGH technologies. Initially, copy-number fluctuations in the genomic segments were assumed to be hallmark of cancer genomes, were assumed to arise by somatic mutations and were assumed to be so detrimental to the normal genomes that they were not expected to vary in the germ-line genomes. However, the technology that revealed these polymorphisms and are currently widely used to study these variations, namely array comparative genome hybridization (array-CGH), are incapable of characterizing their exact long-range structural properties (e.g., involving chromosomal inversions, translocations, segmental deletions, segmental duplications, and large-scale aneuploidy) and are likely to be of limited utility. Importantly, many of these copy-number variations likely cannot be detected, nor can they be positionally and haplotypically located by using any of the conventional short-range non-contextual shotgun sequencing technologies that are currently available. See, e.g., L. Feuk, A. R. Carson, and W. Scherer, "Structural Variation in the Human Genome," *Nature Review Genetics,* 7(2): 85-97, 2006; J. Sebat et al., "Large-Scale Copy Number Polymorphism in the Human Genome," *Science,* 305 (5683): 525-528, 2004.

Array-CGH technologies hybridize two sets of differentially labeled genomic fragments from two different individuals to an array of DNA probes, and determines the copy number differences in the two genomes from a ratio-metric measurement at each of these probe locations. These raw copy-number fluctuation data are further corrected algorithmically by segmenting the genomes into regions of equal copy-number variations, and focusing on the regions where copy-number differs from the expected diploid values.

In another approach, pairs of reads can be obtained from clones, such as fosmids, using a genomic library constructed from the target genome. These reads can then be mapped to the reference human genome using alignment algorithms similar to the ones used in resequencing, and then analyzed to detect putative break-points where copy-numbers are likely to change abruptly from one value to another. While such paired-end sequencing approach can be used to identify limited amount of structural variations (in addition to copy-number variations), they can lack haplotypic disambiguation, and may fail when the long-range rearrangement events span much larger-regions than what can be spanned by the clone length (e.g., a translocation event that moves a segment from one chromosome into another without changing its copy-number).

The difficulties described above undermine the reliability of population-wide genomic studies. Accordingly, at least one of the objectives of various exemplary embodiments of the present disclosure is to address these deficiencies and issues.

SUMMARY OF EXEMPLARY EMBODIMENTS

One of the objects of various exemplary embodiments of the present disclosure is to overcome the deficiencies commonly associated with the prior art as discussed above, and provide exemplary embodiments of the computer-accessible medium, methods and systems for assembling mutually-aligned personalized genome wide maps and haplotype sequences by combining short-rage non-contextual sequence reads and long-range mate-pairs, dilution or optical mapping techniques.

Described herein is an exemplary embodiment of computer-accessible medium having stored thereon computer executable instructions for assembling at least one haplotype sequence of at least one genome. For example, when the executable instructions can be executed by a processing arrangement, the processing arrangement can be configured to perform a procedure including, e.g., obtaining a plurality of randomly located short sequence reads, using at least one score function in combination with constraints based on long range information associated with the at least one genome, generating a layout of all of or a subset of randomly located short sequence reads such that the generated layout is globally optimal with respect to the at least one score function while substantially satisfying the constraints, wherein the at least one score-function is derived from short-range overlap relations among the randomly located short sequence reads, searching coupled with score and constraint dependent pruning to determine the globally optimal layout substantially satisfying the constraints, and generating a whole and/or at least one part of at least one genome wide haplotype sequence or genotype sequence of the at least one genome, converting globally optimal layout substantially satisfying the constraints into one or more consensus sequences, for example.

An exemplary processing arrangement in accordance with the present disclosure can be configured to obtain the randomly located short sequence reads using at least one of, e.g., Sanger chemistry, sequencing-by-synthesis, sequencing-by-hybridization or sequencing-by-ligation. The exemplary processing arrangement also can be configured to obtain data including randomly located short sequence reads using at least one method having at least one type of error source, which, for example, can be, e.g., incorrect base-calls, missing bases, inserted bases and/or homopolymeric compression. The at least one genome can include genomes from a plurality of diseased cells and/or non-diseased cells, at least one individual organism, at least one population, or at least one ecological system, for example. The particular information can include long-range information and the randomly located non-contextual sequence reads can be aided by a score-function encoding particular long range information. The long-range information can be obtained from at least one of a plurality of diseased and/or non-diseased cells, at least one individual organism, at least one population, or at least one ecological system, for example. The exemplary long-range information also can be obtained from, e.g., a mathematical model, existing data, genomic single-molecules, and/or genomic materials amplified and/or modified in a particular manner. The mathematical model can be Bayesian and/or empirical Bayesian.

The long-range information can be obtained from randomly sheared single molecules and/or targeted genomic single-molecules. The long-range information can be, e.g., dilution information or a physical map that is an ordered restriction map, a probe map, and/or a base-distribution map. The long-range information also can be obtained from amplified clones that are analyzed by at least one of restriction activities or an end sequencing procedure. For example, according to certain exemplary embodiments, the long-range information can be obtained from existing data that includes (i) a reference haplotype or genotype whole-genome sequence, (ii) a reference collection of phased, unphased, haplotyped or genotyped sequence contigs, (iii) population-wide whole-genome sequences, and/or (iv) population-wide collections of phased, unphased, haplotyped or genotyped sequence-contigs.

The exemplary processing arrangement can be further configured to store the sequence reads in a tree-type of a data structure having paths that are usable to organize possible arrangements of sequence reads. The sequence reads can be configured to be overlayed, while taking into account the overlaps, containments, and overhangs among consecutive sequence reads in an overlay along at least one path in the arrangement. The exemplary processing arrangement can be further configured to evaluate overlays along the at least one path by utilizing a score function. In addition, the exemplary processing arrangement can be further configured to use the score function to identify the at least one path having relatively low score values with respect to a rank order of the score values of all of the at least one path or plausible bounds. The exemplary processing arrangement also can be further configured to evaluate the score function with respect to at least one of the overlaps, containment and overhangs among a single pair and/or a local collection of pairs of the sequence reads.

In addition, the exemplary processing arrangement can be configured to evaluate the overlaps, containments or overhangs among the sequence reads with unknown orientations, locations, and haplotypic identities. The exemplary processing arrangement can be further configured to evaluate the overlaps, containments or overhangs occurring among the sequence reads from different sequencing technologies, with each different sequencing technology having a respective separate process for performing erroneous reads, for example. The exemplary processing arrangement can be further configured to determine thresholds below which the detected overlaps, containments or overhangs are to be discarded from a further consideration. The exemplary processing arrangement can be configured to determine the values of at least one of the thresholds using a Bayesian method and/or an empirical Bayesian method, and can be further configured to determine the values of at least one of the thresholds using a procedure for controlling false discovery rates.

Further, the exemplary processing arrangement can be configured to evaluate the score function based on a consistency of the score function with respect to the particular long-range information. The exemplary processing arrangement also can be configured to evaluate the score function based on a consistency of the score function with respect to the particular long-range information by determining a local alignment with an alignment score, for example. The exemplary processing arrangement can be further configured to determine the score-function using a dynamic programming procedure for a local alignment with an alignment score. The exemplary processing arrangement also can be configured to determine the score function by using at least one alignment score parameter obtained by, e.g., a learning procedure, heuristics and/or a Bayesian-based design. Further, the exemplary processing arrangement can be configured to select at least one of the relatively best scoring arrangements of the sequence reads to determine a corresponding multiple sequence alignment that can be combined to generate the at least one whole-genome haplotypic sequence, for example.

The exemplary randomly located short sequence reads can be generated using Sanger chemistry, sequencing-by-synthesis, sequencing-by-hybridization and/or sequencing-by-ligation, for example. The exemplary randomly located short sequence reads may also be generated using a method having at least one error. For example, the error can be incorrect base-calls, missing bases, inserted bases and/or homopolymeric compression.

Also described herein is an exemplary embodiment of a procedure for assembling at least one haplotype sequence of at least one genome. The exemplary method can include, for example, obtaining a plurality of randomly located short sequence reads, using at least one score function in combination with constraints based on long range information associated with the at least one genome, generating a layout of all of or a subset of randomly located short sequence reads such that the generated layout is globally optimal with respect to the at least one score function while substantially satisfying the constraints, wherein the at least one score-function is derived from short-range overlap relations among the randomly located short sequence reads, searching coupled with score and constraint dependent pruning to determine the globally optimal layout substantially satisfying the constraints, and generating a whole and/or at least one part of at least one genome wide haplotype sequence or genotype sequence of the at least one genome, converting globally optimal layout substantially satisfying the constraints into one or more consensus sequences, for example. An exemplary procedure according to the present disclosure can also include displaying and/or storing the particular information and/or a whole or one or more parts of at least one genome wide haplotype sequence in a storage arrangement in a user-accessible format and/or a user-readable format.

In addition, a system for assembling at least one haplotype sequence of at least one genome according to another exemplary embodiment of the present disclosure can be provided. The exemplary system can include a processing arrangement, which, when executed, can be configured to perform at least one procedure including: obtaining a plurality of randomly located short sequence reads, using at least one score function in combination with constraints based on long range information associated with the at least one genome, generating a layout of all of or a subset of randomly located short sequence reads such that the generated layout is globally optimal with respect to the at least one score function while substantially satisfying the constraints, wherein the at least one score-function is derived from short-range overlap relations among the randomly located short sequence reads, searching coupled with score and constraint dependent pruning to determine the globally optimal layout substantially satisfying the constraints, and generating a whole and/or at least one part of at least one genome wide haplotype sequence or genotype sequence of the at least one genome, converting globally optimal layout substantially satisfying the constraints into one or more consensus sequences, for example.

These and other objects, features and advantages of the present disclosure will become apparent upon reading the following detailed description of exemplary embodiments of the invention, when taken in conjunction with the appended claims.

BRIEF DESCRIPTION OF THE DRAWINGS

Further objects, features and advantages of the invention will become apparent from the following detailed description taken in conjunction with the accompanying figures showing illustrative embodiments of the invention, in which

FIG. 2A is a representation of exemplary computer code for the high-level procedure in accordance with an exemplary embodiment of the present disclosure;

FIG. 2B is a representation of the exemplary computer code for the node expansion procedure using the branch-and-bound method;

FIG. 6 is a graph of an example of a *Brucella suis* contig length distribution in accordance with certain exemplary embodiments of the present disclosure;

FIG. 8 is an example of a table providing comparison of results from an example in accordance with the present disclosure and five other sequence assemblers;

Figure 1A:
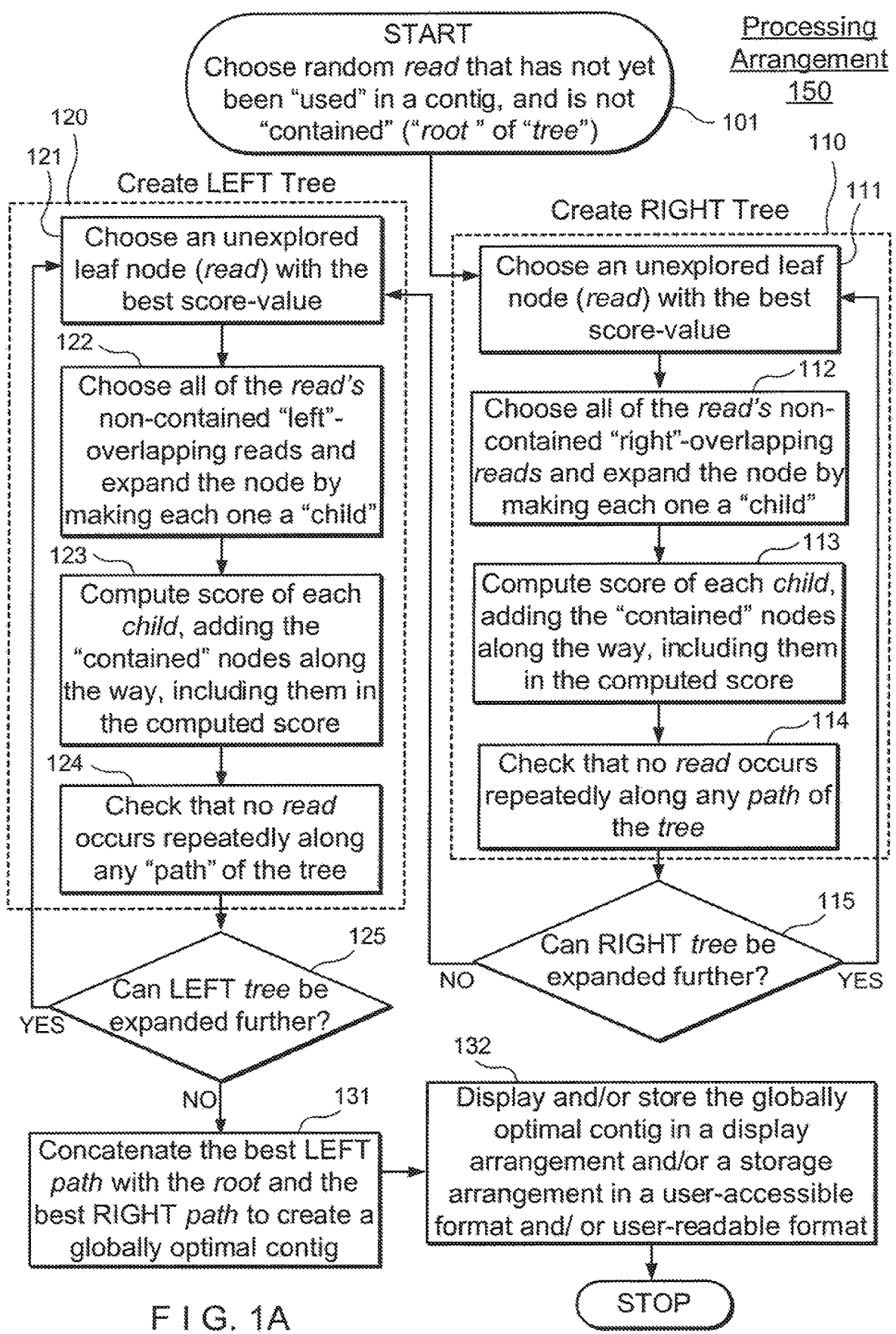
FIG. 1A is a combination of a block diagram and a flow diagram of a method for generating at least one genome wide haplotypic sequence in accordance with an exemplary embodiment of the present disclosure.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

According to exemplary embodiments of the present disclosure, exemplary optical mapping procedures can be used to produce long-range information in the form of single-molecule-based ordered restriction maps. Such information, which, when analyzed in conjunction with short-range non-contextual sequence reads (arising, not exclusively, from a diverse group of new generation sequencing technologies), can be used to assemble the sequence reads correctly into a genome wide personalized haplotype sequence. Accordingly, described herein are exemplary embodiments of methods, computer-accessible medium, and systems for assembling mutually-aligned personalized genome wide maps and haplotype sequences using short-rage non-contextual sequence reads and long-range optical mapping techniques. These exemplary methods, computer-accessible medium, and systems may provide powerful strategies that may facilitate statistical combinations of disparate genomic information and/or exemplary chemical protocols that may, in parallel, manipulate and interrogate a large amount of sequencing, mapping and disease association data in various environments (e.g., personalized medicine, population studies, clinical studies, pharmacogenomics, etc.).

Exemplary embodiments of the methods, computer-accessible medium, and systems according to the present disclosure for assembling short-range sequence reads with assistance from long-range low-resolution data, e.g., genome wide optical maps can be provided for use in generating a genome wide haplotype sequence, e.g., the nucleotide sequence of a whole diploid genome at the haplotypic level. Various exemplary applications of such exemplary methods, computer-accessible medium, and systems can include, but are not limited to, analyzing patient genomes to predict susceptibility to various genetic or genomic diseases, or analyzing patient genomes to diagnose genomic instability and mutations as the basis of cancer, or analyzing patient genomes, with or without other auxiliary data, to individualize therapeutic interventions for the patient, for example. Exemplary embodiments of the present disclosure can also have agricultural and biomedical applications in drug-or-vaccine discovery, understanding behavior of a cell in an altered state (e.g., cancer, neuron-degeneration, or auto-immune disease, etc.), genetically modifying a natural wildtype organism, genetic engineering, etc. Other exemplary applications may include, e.g., understanding neural behavior, evolutionary processes, and genome evolution and aging.

As discussed herein, for example, advances in genomics, particularly in the development of new generation sequencing technologies and in the use of optical mapping to generate a genome wide haplotypic long-range information via single-molecule restriction patterns, have created new opportunities for assembly procedures to create genome-wide haplotypic sequences. Such exemplary sequences can be used for locating common variants in polymorphisms, carrying out association studies, identifying many of the genes commonly implicated in disease, and elucidating many of the cellular pathways upon which they act. In order to utilize these opportunities, exemplary embodiments of the present disclosure can provide robust, efficient, and inexpensive technologies, systems, procedures, and processes that can assemble short-range non-contextual sequence-reads into validated genome wide haplotype sequences, which can facilitate a review of genomic variations at multiple scales and across multiple individuals and species. Accordingly, described herein are exemplary embodiments of the methods, computer-accessible medium, and systems, for assembling non-contextual sequence-reads into genome wide haplotype sequences.

The shotgun sequence assembling problem can generally be considered to be challenging for the following reasons: (1) in the absence of locational or contextual information and in the presence of low-quality base-call, the possible arrangements of overlay of all the sequence-reads are likely and should be exhaustively considered, and (2) the shotgun sequence-reads incorporate short-range information, and thus are incapable of identifying which of these arrangements would be valid. If a "goodness" score can be defined for a particular arrangement of sequence reads, then the shotgun-sequence assembly problem can be formulated as a constrained global optimization problem, which would choose the "best" arrangement from, potentially, a multitude of many possible arrangements of sequence-reads.

For example, if the "goodness" score can itself be defined in terms of validity of sub-arrangements, then it can be defined in terms of an empirical-Bayes or Bayes-like formulation, and the optimization of such a score function should provide a high level of confidence that the sequence reads are assembled correctly. Such score function can be computed or determined in different ways, such as, e.g., by the significance of the overlaps selected in the assembly, by the significance of mate-pair constraints in the arrangements of the reads selected in the assembly, by the concurrence of the assembled consensus sequence with a reference sequence, or, as may be preferred in certain exemplary embodiments according to the present disclosure, by the agreement of the assembled consensus sequence with single-molecule restriction map (checked in terms of in silico computed restriction maps).

Such global optimization problems are likely to be computationally intractable and cannot be correctly solved by a "greedy" procedure, which will often get stuck in certain local maxima for the score function and not produce a valid sequence assembly.

Exemplary embodiments of the present disclosure, instead, can use a global search-method with branch-and-bound heuristics (or beam search) to contain the complexity of the procedure. Such exemplary procedure can facilitate a location of the globally optimal solution and hence achieve a high level of accuracy. To achieve a high computational space and time efficiency, the exemplary procedure can prune out (e.g., identify and reject) branches leading to "unpromising" solutions (e.g., solutions for which there is a relatively low level of expectation for success of achieving an acceptable level of accuracy) quickly and should rely on the availability of sufficiently high coverage and good quality long-range genomic data (e.g., high coverage optical mapping data with good digestion rate and size accuracy). According to various exemplary embodiments of the present disclosure, the efficiency may require optical maps with respect to more than one enzyme.

In certain exemplary embodiments of the present disclosure, accuracy and validity of the assembled consensus sequence may rest upon the fidelity of the underlying models describing the "error processes," involved in the long-range genome information and sequence reads, and reflected in the score. The exemplary score function can thus combine Bayesian likelihood obtained from the prior distributions derived from the model and various penalty functions (corresponding to various constrains), for example. In certain exemplary embodiments of the present disclosure, various relatively simple but meaningful heuristic score functions and penalty functions may be employed. These functions can be provided by a human, be learned from the data by any generally known "machine learning" approach, or by an empirical Bayes approach that derive the priors from the data themselves. For example, an empirical-Bayes method may be used to decide the statistics and thresholds (e.g., null-model, threshold, p-values, base- or sequence-quality), thus making the system independent from the underlying technology while being able to mix-and-match different technologies.

According to further exemplary embodiments of the present disclosure, in addition to score functions based on certain modeled, learnt or known models, other information may be used (e.g., optical maps, mated pairs, base-content, homologous reference sequences, etc.), which can sharpen and improve the score function causing the algorithm to behave more efficiently.

An exemplary procedure according to the present disclosure may use differing technologies, including those for which no known models of error processes heretofore exist. For example, there may be available two different kinds of sequence-reads with two different length parameters, from two different technologies, and subjected to two different classes of error processes. In this example, these two different technologies may be, e.g., 454/Roche and Solexa/Illumina; 454 sequence reads may be of length 500 bp on the average and Solexa sequence reads, 50 bp; 454 may have homo-polymer compressions, while Solexa may have seriously low-quality base calls beyond a certain length, for example. From the data itself, however, it may be possible to create a null-model of false-overlaps, and these distributions can then be used in an exemplary score function.

A score-function in accordance with the present disclosure can be used to guide the manner in which the short-sequence reads are arranged and further combined into haplotype sequence information (either in its entirety or in parts in terms of contigs).

For example, certain techniques that can be used by an exemplary procedure to improve efficiency can be described as being of different types: e.g., (a) careful selection of the experimental parameters used in collecting the long-range experimental data; and (b) estimation of tight bounds on the statistically less significant score values, which allow early and aggressive identification and rejection of unpromising regions/directions in sequence assembly. Thus, an exemplary procedure can be implemented to work quickly by dove-tailing between local (short sequence-reads) and global (long-range maps and haplotypic) information. Such exemplary procedure can organize the sequence-read arrangements in a tree-type structure, which can be periodically trimmed to terminate the relatively low-scoring and unpromising directions, by using the long-range information in the score function to recognize those paths in the tree that would be inconsistent with the long-range information, for example. Since the tree can also organize the long-range information along the paths, errors that are in the long-range information should automatically get discarded by this process. For example, if the long-range information used is single-molecule optical maps, then while the optical maps may ensure that the assembly of the sequence-reads proceed along the correct directions, the assembled sequences can identify the incorrect single molecule maps, e.g., those with optical chimerism, quickly and force them to be discarded immediately.

Exemplary embodiments of procedures according to the present disclosure can be tuned heuristically (e.g., size of a priority queue used in the branch-and-bound) to obtain, e.g., the best possible computational complexity and resource consumptions as a function of specific error parameters and required accuracy. For example, this procedure can automatically provide a way to exploit underlying 0-1 laws in these technologies, such as, for example, a law that states that there exist certain error parameter thresholds (for the error processes in sequencing and mapping) below which the probability of assembling sequence-reads correctly is relatively close to zero, while above this threshold, the correct assembly probability sharply jumps to be relatively close to one. Such laws can have strong implications for the design of the underlying technologies, choice of the component technologies, parameters used in the technologies and in selecting the manner in which the exemplary procedure operates.

An exemplary procedure can parallelize in a straightforward manner, as multiple regions can be explored simultaneously by different processors, with search trees starting with roots at a relatively small number of randomly selected seeds (sequence-reads from which a local assembly is initiated).

With reference to FIG. 1A which shows a combination of a block diagram and a flow diagram of a method for generating at least one genome wide haplotypic sequence in accordance with an exemplary embodiment of the present disclosure, further details regarding the procedure according to certain exemplary embodiments of the present disclosure are provided as follows.

This exemplary procedure can be performed by a processing arrangement 150. For example, processing arrangement 150 can be, entirely or a part of, or include, but not limited to, a computer that includes a microprocessor, and using instructions stored on a computer-accessible medium (e.g., RAM, ROM, hard drive, or other storage device).

In 101, the processing arrangement 150 chooses a random read that has not yet been "used" in a contig, and is not "contained." This read is the root of a tree.

In 111, the processing arrangement 150 can start to generate the RIGHT tree (sub-procedure 110) by choosing an unexplored leaf node (read) with the best score-value. Next, in 112, the processing arrangement 150 can select most or all of the read's non-contained "right"-overlapping reads and expands the node by making each one of them a child. In 113, the processing arrangement 150 can compute the scores of each child, adding the "contained" nodes along the way, while including them in each computed scores. The processing arrangement 150, in 114, can then check that no read occurs repeatedly along any path of the tree.

In 115, the exemplary processing arrangement 150 can inquire whether the RIGHT tree can be expanded further. If the answer determined by the exemplary processing arrangement 150 in 115 is "yes", then the exemplary procedure can return to 111, in which the processing arrangement 150 can continue to create the RIGHT tree (sub-procedure 110) by choosing an unexplored leaf node (read) with the best score-value. If the answer determined by the exemplary processing arrangement in 115 is "no", then the exemplary procedure proceeds to step 121, in which the exemplary processing arrangement 150 can begin to create the LEFT tree (exemplary sub-procedure 120) by choosing an unexplored leaf node (read) with the best score-value.

After selecting an unexplored leaf node (read) with the best score-value in 121, the exemplary processing arrangement 150, in 122, can then choose all of the read's non-contained "left"-overlapping reads and expand the node by making each one of them a child. In 123, the exemplary processing arrangement 150 can compute the scores of each child, adding the "contained" nodes along the way, while including them in each computed score. The exemplary processing arrangement 150, in 124, can then check that no read occurs repeatedly along any path of the tree.

Next, in 125, the exemplary processing arrangement 150 can inquire whether the LEFT tree can be expanded further. If the answer determined by the exemplary processing arrangement 150 in 125 is "yes", then the exemplary procedure can return to 121, in which the exemplary processing arrangement 150 can continue to create the LEFT tree (sub-procedure 120) by choosing an unexplored leaf node (read) with the best score-value. If the answer determined by the exemplary processing arrangement 150 in 125 is "no", the exemplary procedure can proceed to step 131, in which the exemplary processing arrangement 150 can concatenate the best LEFT path with the root and the best RIGHT path to create a globally optimal contig. The exemplary procedure can then continue to step 132, in which the exemplary processing arrangement 150 can display and/or store the globally optimal contig in a display arrangement and/or a storage arrangement in a user-accessible format and/or user-readable format. The exemplary procedure can then continue to 139, in which it is stopped by the processing arrangement 150.

The exemplary processing arrangement 150 can be provided with or include an input arrangement, which can include, e.g., a wired network, a wireless network, the internet, an intranet, a data collection probe, a sensor, etc. Further, the exemplary processing arrangement 150 can be provided with or include an output arrangement, which can include, e.g., a wired network, a wireless network, the internet, an intranet, etc., in addition to a display arrangement and/or a storage arrangement in which data can be stored in a user-accessible format and/or user-readable format.

Figure 1B:
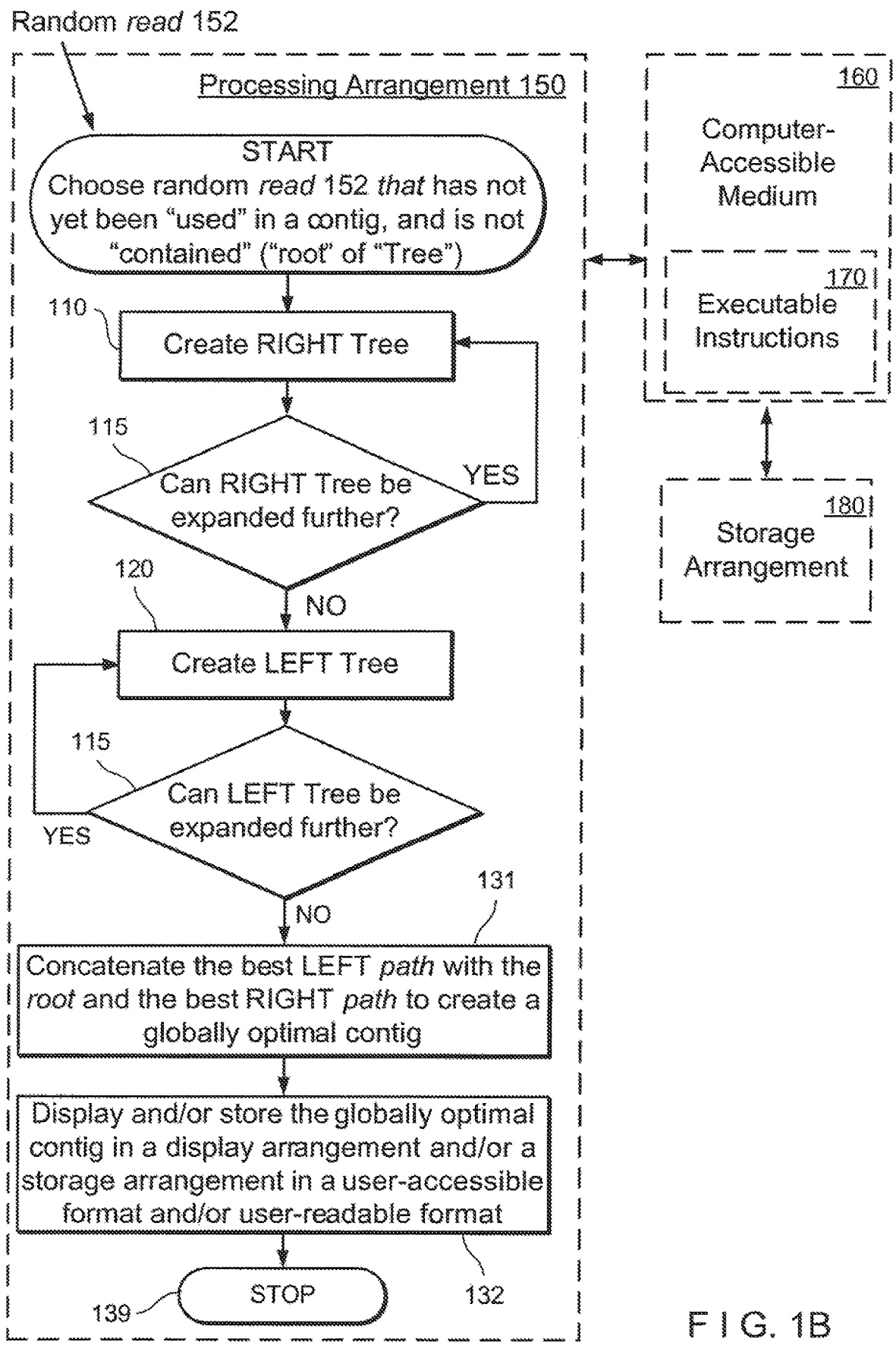
FIG. 1B is a combination of a block diagram and a flow diagram of a system which is configured to execute the exemplary method of FIG. 1A.

FIG. 1B shows a diagram of a combination of the exemplary procedure of FIG. 1A and of an exemplary system which is configured to execute the exemplary procedure of FIG. 1A. As described above, this exemplary procedure can be performed by a processing arrangement 150, which, for example, can be, entirely or a part of, or include, but not limited to, a computer that includes a microprocessor, and using instructions stored on a computer-accessible medium (e.g., RAM, ROM, hard drive, or other storage device).

As shown in FIG. 1B, e.g., a computer-accessible medium 160 (e.g., as described herein above, storage device such as hard disk, floppy disk, memory stick, CD-ROM, RAM, ROM, etc., or a collection thereof) can be provided (in communication with the processing arrangement 150). The computer-accessible medium 160 can contain executable instructions 170 thereon. In addition or alternatively, a storage arrangement 180 can be provided separately from the computer-accessible medium 160, which can provide the instructions to the processing arrangement 150 so as to configure the processing arrangement to execute certain exemplary procedures, processes and methods, as described herein above.

For example, the exemplary processing arrangement 150 can choose and/or receive a random read 152 choosing a random read that has not yet been "used" in a contig, and is not "contained". This read is the root of a tree. In step 110, the processing arrangement 150 creates the RIGHT tree. In 115 (similarly as in FIG. 1A), the exemplary processing arrangement 150 can inquire whether the RIGHT tree can be expanded further. If the answer determined by the exemplary processing arrangement 150 in step 115 is "yes", then the exemplary procedure returns to 110, in which the processing arrangement 150 continues to create the RIGHT tree. If the answer determined by the exemplary processing arrangement in 115 is "no", then the exemplary procedure proceeds to 120, in which the exemplary processing arrangement 150 can create the LEFT tree by choosing an unexplored leaf node (read) with the best score-value, in a similar manner as provided above with respect to FIG. 1A.

In 115, the exemplary processing arrangement 150 inquires whether the LEFT tree can be expanded further. If the answer determined by the exemplary processing arrangement 150 in step 115 is "yes", then the exemplary procedure can return to step 120, in which the exemplary processing arrangement 150 can continue to create the LEFT tree by choosing an unexplored leaf node (read) with the best score-value. If the answer determined by the exemplary processing arrangement 150 in 115 is "no", the exemplary procedure can proceed to step 131, in which the exemplary processing arrangement 150 can concatenate the best LEFT path with the root and the best RIGHT path to create a globally optimal contig. The exemplary procedure then continues to 132, in which the exemplary processing arrangement 150 displays and/or stores the globally optimal contig in a display arrangement and/or a storage arrangement in a user-accessible format and/or user-readable format. The exemplary procedure can then proceed to 139, in which it is stopped by the processing arrangement 150.

As described above, an exemplary procedure can use branch-and-bound (or beam search) to avoid immense space and time complexity. An exemplary procedure can also use depth-first search interval schemes to see if a read occurs repeatedly along a path. Furthermore, it may only check right- or left-overlapping properties between two reads while expanding the root, since checking just overlapping relation for the non-root node suffices. It is preferable to avoid reads from the best right path to be included in any left path. Thus, certain exemplary book-keeping can be done to keep track of "used," "explored," "overlapping," and "contained" relationships, for example.

FIGS. 2A and 2B shows representations of exemplary computer executable instructions (computer code) for an exemplary procedure in accordance with certain exemplary embodiments of the present disclosure.

In particular, FIG. 2A illustrates an exemplary representation of exemplary computer code 210 for a high-level procedure 211 in accordance with an exemplary embodiment of the present disclosure. As shown in this example, two particular data structures can be maintained: a forest of double-trees (D-tree) F 212 and a set of contigs C 213. Upon execution of each step 215, a new D-tree is initiated from one of the remaining reads left in the set of available reads B 214. Once the construction of the D-tree is completed, the associated contig is created and stored in the set of contigs C 213. Next the layout for this associated contig is computed and its reads are removed from the set of available reads B 214. This exemplary process continues as long as there are reads left in the set of available reads B 214. According to certain exemplary embodiments of an exemplary process, both the forest of D-trees F 212 and the set of contigs C 213 can be kept and updated in the pseudocode. According to other exemplary embodiments of an exemplary process, however, after the layout of a contig is computed, there may be no particular reason to keep the full D-tree stored in memory, especially, where, e.g., there may be certain memory restrictions or requirements.

FIG. 2B illustrates an exemplary representation of exemplary computer code 220 for a node expansion procedure using an exemplary branch-and-bound procedure that can be used in the exemplary high-level procedure 211 of FIG. 2A. The amount of exploration and resource consumption (pruning) can be controlled by, e.g., the two parameters K 212 and T 213, where K 212 is the max number of candidate solutions allowed in the queue at each time step, and T 213 is the percentage of top ranking solutions compared to the current optimum score. According to this example, at each iteration 214, the queue can be pruned such that its size is ≤max(K, T). While K 212 can remain fixed at each iteration of the expansion routine, the percentage of top ranking solutions can dynamically change over time. Accordingly, more exploration can be performed when there are many solutions to evaluate having a similar score, for example.

Figure 3:
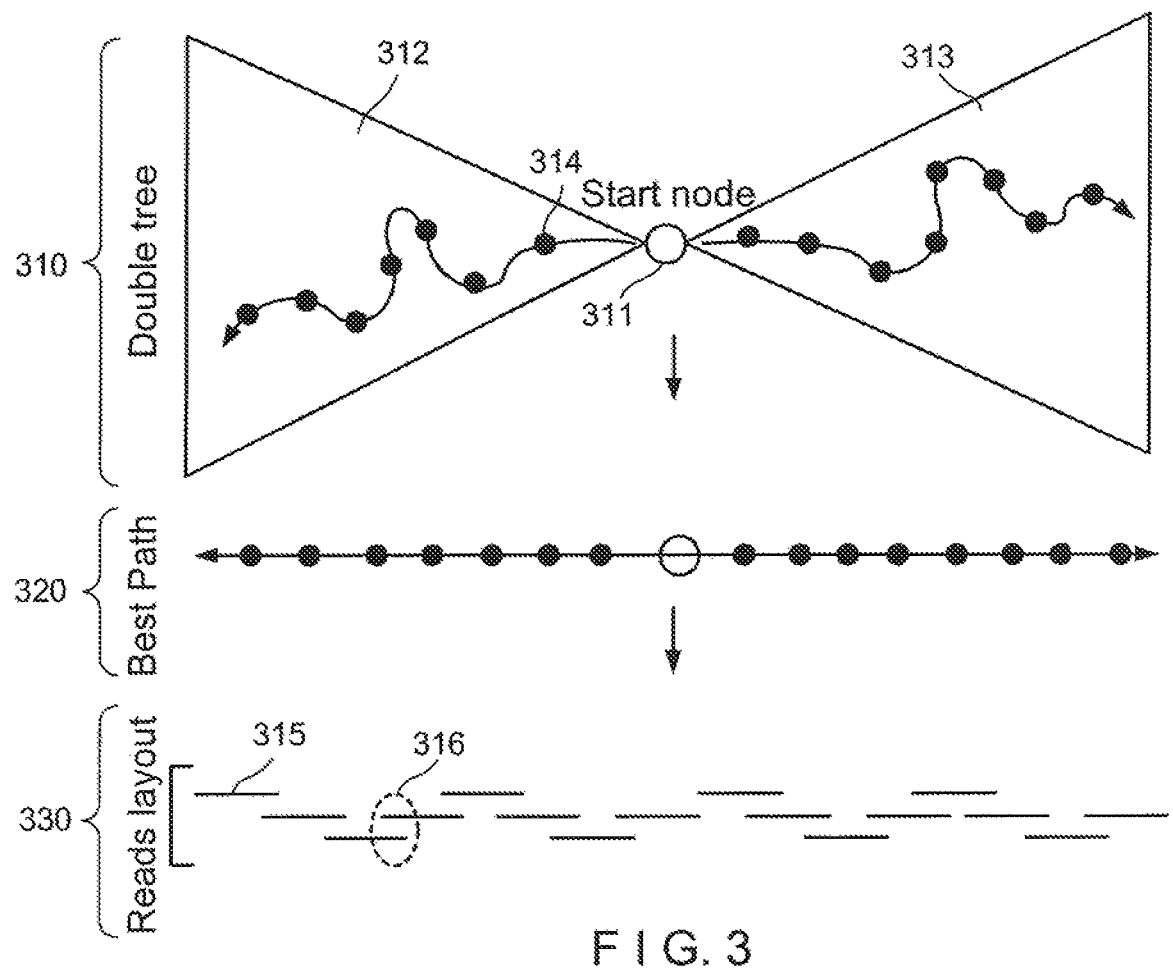
FIG. 3 is an illustration of procedure for a contig construction associated with the exemplary procedure shown in FIG. 1A.

FIG. 3 shows an illustration of an exemplary procedure that can be involved in the construction of an exemplary contig. As shown, a double tree 310 can be created from a start node 311, with each tree 312, 313 having nodes 314 based on reads 315, as is shown in reads layout 330. The potentially exponential size of each tree 312, 313 can be controlled by using certain exemplary structures of an assembly problem that permits a quick pruning of many redundant branches of a tree. For example, according to certain exemplary embodiments of the present disclosure, substantial pruning can be done using only local structures of the overlap relations 316 among the reads 315—e.g., it may not be prudent to spend time on expanding nodes that can create a suffix-path of a previously created path, as no information is lost by delaying the expansion of the last node/read involved in such an exemplary "transitivity" relation, which can happen, e.g., whenever there is a transitivity edge between three or more consecutive reads.

Figure 4:
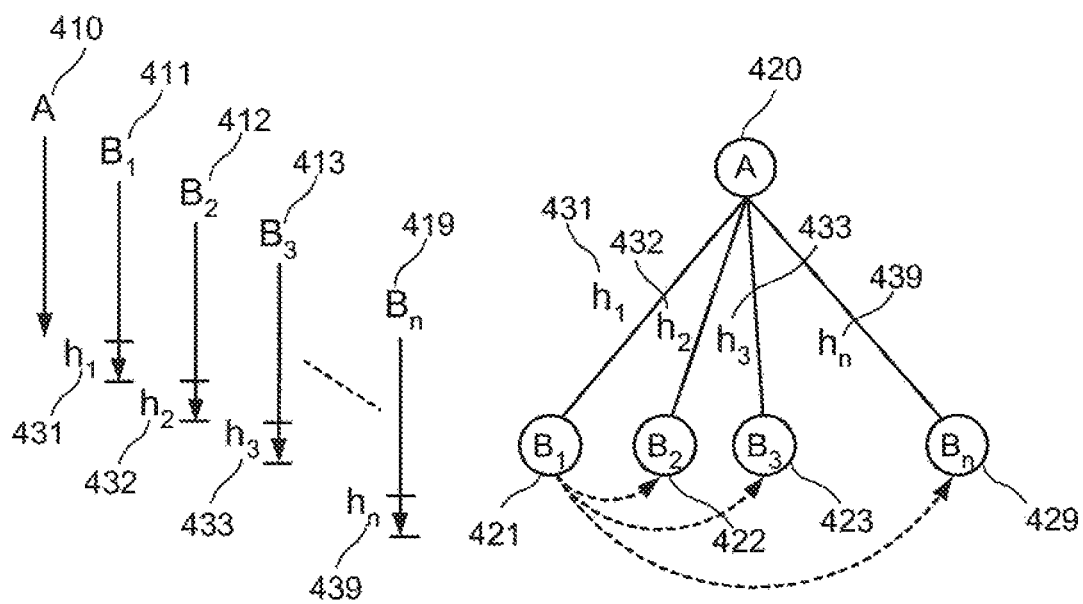
FIG. 4 is an example of a transitivity pruning procedure in accordance with certain exemplary embodiments of the present disclosure.

FIG. 4, for example, shows an exemplary transitivity pruning procedure in accordance with certain exemplary embodiments of the present disclosure. In this example, reads A 410, $B_1$ 411, $B_2$ 412, $B_3$ 413 . . . , $B_n$ 419 are n+1 reads with the exemplary layout shown in FIG. 4. The local structure of the resulting exemplary tree will have node A 410 with n children nodes $B_1$ 421, $B_2$ 422, $B_3$ 423 . . . , $B_n$ 429. Since, as shown in this example, read $B_1$ 411 can overlap reads $B_2$ 412, $B_3$ 413 . . . , $B_n$ 419, these nodes can appear as children of node $B_1$ 421 at the next level in the tree. So the expansion of nodes $B_2$ 422, $B_3$ 423, . . . , $B_n$ 429 can be delayed because of the overlap of their corresponding reads with read A 410 can depend on read $B_1$ 411. The expansion can be similar for nodes $B_2$ 422, $B_3$ 423 . . . , $B_n$ 429. It can be possible for this exemplary pruning procedure to reduce a full tree structure into a linear chain of nodes. Additional optimization can be performed, e.g., by evaluating the children in an increasing order of hangs (e.g., h1 431≤h2 432≤h3 433≤ . . . ≤hn 439, where hi is the size of the hang for read Bi, the hang being the read portion that is not involved in an overlap). This exemplary ordering can give a higher priority to, e.g., reads with a higher overlap score.

According to exemplary shotgun sequencing projects, the sizes of the fragments generated can be carefully controlled, thus providing statistical information (e.g., mean and standard deviation) about the distance between the two reads sequenced from the ends of the same fragment (which can be called, e.g., "paired-ends" or "mate-pairs"). According to certain exemplary embodiments of the present disclosure, within the assembly, mate-pair reads can be placed at a distance consistent with the size of the library from which they originated and be oriented towards each other. Reads that do not satisfy these constraints may not have their corresponding nodes expanded so that the sub-trees that could have otherwise been generated by these nodes/reads are pruned.

The score function (or components of it), in a relatively simple possible setting can be based on the short-range information. For example, along a path, consecutives short-reads clearly may overlap, but they may also satisfy other "derived" relationships. For example, provided that the genomic coverage is higher than 3 (i.e., 3× coverage or higher), it could be expected that if sequence-reads A and B overlap, and B and C overlap, then there is a relatively high probability that A and C also overlap. Thus, certain exemplary embodiments of the present disclosure can start with a very simple score function: An exemplary score function can use a "weighted transitivity" score—e.g., along a path, if read A overlaps read B, and read B overlaps read C, it can score those overlaps strongly if in addition A and C also overlap.

An exemplary score function can be expressed as follows:

```
If (Overlap(A,B) && Overlap(B,C)) {
    Score(A, B, C) =
    [Score(A,B) + Score(B,C)]+ [Overlap(A,C) ? Score(A,C) : 0]
}
```

A simple generalization for higher coverage may be apparent to one having ordinary skill in the art in view of the teachings of the present disclosure. For example, scores may not resolve repeats or haplotypic variations. Thus, for this information to be properly accounted for, an exemplary score can have to be augmented with components based on long-range information (e.g., spanning a region of 150 Kb or greater, or 100 Kb or greater), for example.

Certain exemplary penalty functions can be used in the score to prune out (e.g., identify and reject) anomalous paths in an exemplary tree organizing the arrangements of sequence reads. For example, a path can be considered as an unlikely assembly solution if it overlays sequence reads in such a way that at certain locations, the local coverage far exceeds the global average coverage, and violates what can be expected in terms of the Poisson (or over-dispersed Poisson, Binomial, etc.) distribution of the coverages. In another example, a path can be anomalous and thus, penalized, if, in the multiple sequence alignment induced by the overlays of the sequence-reads along this path, there exist regions with distributions of misaligned bases and gaps that are statistically significantly inconsistent with what could be expected by the distributions of single nucleotide polymorphisms and/or indel polymorphisms, etc. There can be other local score functions and penalty functions that are similar to the ones described herein above, as may be obvious to a one having ordinary skill in the art in view of the teachings of the present disclosure.

In certain exemplary embodiments of the present disclosure, while the local components of the score, the transitivity and mate-pair pruning, and the penalty functions may not be sufficiently strong to validate a sequence assembly or disambiguate the haplotypic variations, they can provide for eliminating an obviously and/or clearly bad and/or inaccurate assembly very early in the procedure with significantly simple efficient computation, for example. In addition, it has been demonstrated that they can often be sufficiently powerful to create reasonably large-sized contigs (and/or even full sequences for small bacteria-sized genomes), thus making the relatively more computationally intensive steps being executed far more rarely than they may be otherwise executed.

According to further exemplary embodiments of the present disclosure, long-range information, e.g., what information can be obtained from optical map alignment, reference sequence, base distribution frequency, and/or mated-pair distances, can be used to derive additional exemplary reward/penalty Bayesian terms in the over-all score function. These exemplary terms can ensure and/or substantially ensure that, e.g., a reasonably long contig that may be suggested by a subpath of a path in the tree be consistent with the corresponding long-range information.

Figure 5:
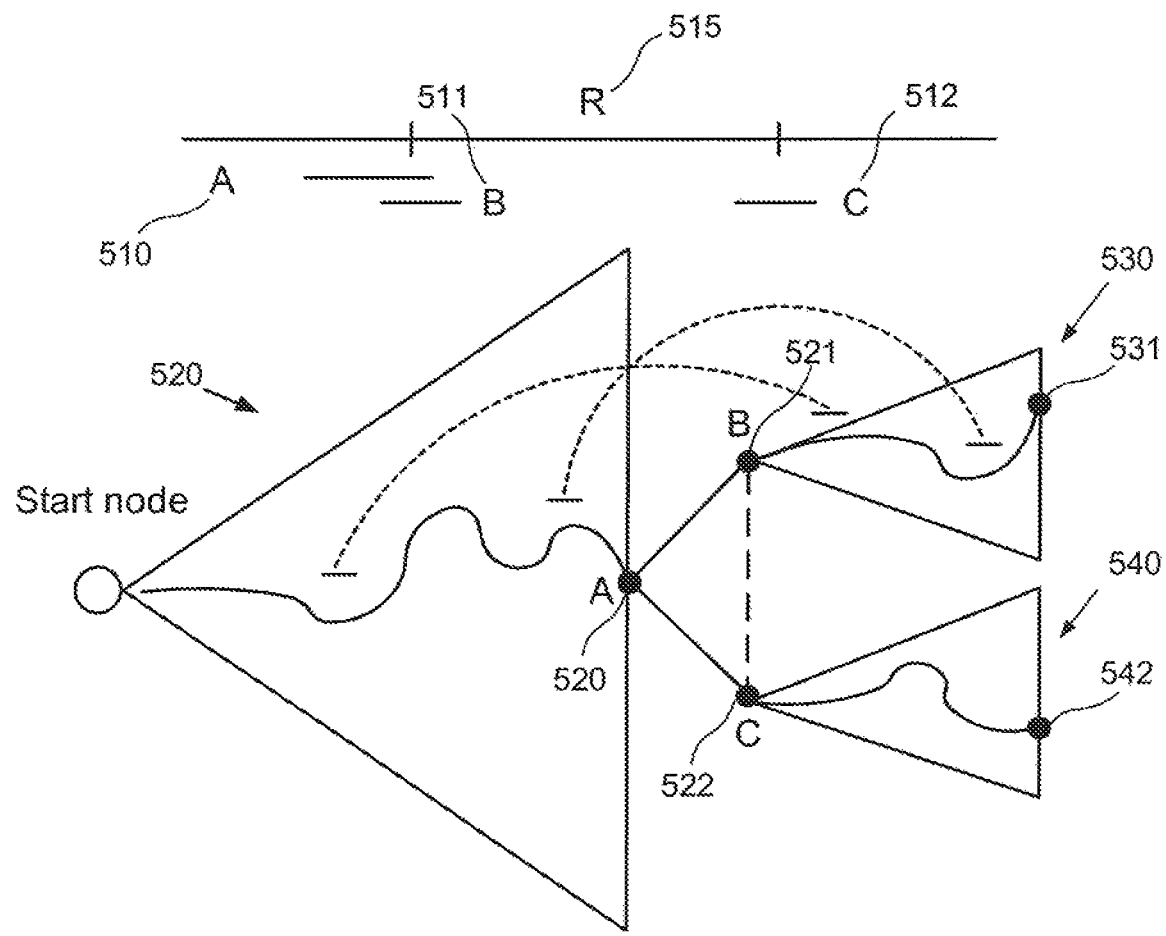
FIG. 5 is an illustration of a diagram of an exemplary look-ahead procedure in accordance with an exemplary embodiment of the present disclosure.

For example, FIG. 5 shows an illustration of a diagram of an exemplary lookahead procedure in accordance with certain exemplary embodiments of the present disclosure For example, in this figure, mate-pair data can be used to disambiguate repeat regions of the layout as it is assembled. A potential repeat boundary location R 515 between reads A 510, B 511 and C 512 can be generated. For example, if read A 510 overlaps both reads B 511 and C 512, but read B 511 and read C 512 do not overlap each other, the missing overlap between reads B 511 and C 512 can be a possible repeat-boundary location R 515, making certain pruning decisions impossible. However, according to certain exemplary embodiments of the present disclosure, it is possible to resolve this scenario by looking ahead into possible layouts generated by the reads B 511 and C 512 and keeping the node (e.g., node 531 or node 542) that generates a layout with the least number of unsatisfied constraints (e.g., consistent with mate-pair distances or restriction fragment lengths from optical maps). For example, as shown in FIG. 5, two subtrees 530, 540 can be generated—one for node B 531 and the other for node C 542. The size of each subtree can be controlled by, e.g., a parameter W, which can be the maximum height allowed for each node in the tree. For genomes with short repeats, a small value for W can be sufficient to resolve most repeat boundaries, and can be estimated, e.g., from a k-mer analysis of the reads. With genomes of high complexity (e.g., one with a complex family of LINEs, SINEs and segmental duplications with varying homologies), relatively higher values of W can be used and be estimated adaptively. Once the two (or more) subtrees are constructed, for each node in the path, its pairing mate (if any) can be searched to collect only those mate-pairs crossing a connection point between the subtree(s). The best path can then be selected based on the overlap score. The quality of each path can be evaluated by, e.g., a reward/penalty function corresponding to mate-pair constraints.

As another example, a subpath in a path of the tree of sequence-read-arrangements and the in silico ordered restriction maps that could be suggested by this subpath can be considered. Such in silico maps can be determined or computed, e.g., only approximately by noting the occurrences of the restriction patterns among the sequence reads along the subpath, and inferring the base-pair distances among the consecutive detected sites. Certain errors may occur in such in silico maps because of the homopolymeric compressions, such as, e.g., incorrect or low-quality base-calls, loss of synchronizations in reaction steps, etc. Accordingly, the statistical properties of such computationally induced errors can be identified and incorporated into the score function, using, e.g., a Bayesian algorithm/procedure in a manner that may be known to a person having ordinary skill in the art in view of the teaching provided in the present disclosure. Thus, for explanatory purposes, the following description of an exemplary embodiment according to the present disclosure assumes an error-free case.

According to such exemplary embodiments of the present disclosure, it can thus be assumed that a Bayesian prior starts with a subpath that leads to an error-free valid in silico ordered restriction map, and that the corresponding long-range information can be presented by an optical map of a single-molecule genomic DNA. This can be consistent with a hypothesized in silico map upon various misalignments being explained in terms of error processes governing, e.g., partial digestion, false optical cuts, chimerisms, sizing errors, etc. The better or best alignments and the corresponding score values can be computed using, e.g., dynamic programming. If several single-molecule optical maps align well with many subpaths along a path in a tree, organizing the sequence reads, then certain pairs of optical maps can overlap and have alignments in diose overlapping regions. These global multiple alignments among the optical maps can be evaluated, e.g., for their consistencies and included in the over-all score function.

For example, the event of a cut missing in the optical map may be modeled as a Bernoulli process, yielding a parameter called partial digestion rate $p_c<1$. The corresponding term in the score function would be $\ln 1/(1-p_c)$. Similarly, assuming false-cuts to be distributed in terms of a Poisson process, with parameter $p_f$, the corresponding term in the score function would be $\ln 1/p_f$. The sizing error can be modeled in terms of a Gaussian distribution with a mean a and standard deviation s. If the measured length is 1, then the corresponding score would be given by a weighted sum-of-square function, where the corresponding term would be $(1-a)^2/s^2$. Details of the overall score function, and how to efficiently compute such using a dynamic programming approach can be understood to a person having ordinary skill in the art in view of the teachings of the present disclosure.

Long-range information, such as, e.g., single-molecule-based optical ordered restriction maps, and sequence-reads, can be represented approximately by various geometric hashing schemes and stored in an easy-to-search hash table, for example. According to certain exemplary embodiments of the present disclosure, the overall organization of the data structures, the software and the implementation involving cycles of search-alignment-score-prune-and-unfold can follow standard software engineering practice.

Similar schemes, such as, e.g., replacing or augmenting optical maps, with mated pairs, ordered probe maps, sequencing-by-hybridization spectra, reference maps, population-wide polymorphism data, targeted maps of genomic regions, maps of base-pair composition distributions along a genomic region, maps of distributions of various physical or chemical properties (e.g., purine-pyrimidines, codons, affinities to other molecules, Gibbs free-energy, stacking energy, etc.) along a genomic region, can also be implemented in accordance with certain exemplary embodiments of the present disclosure.

The description of certain exemplary embodiments of the present disclosure provided herein include an example of implementations of the procedural models using a relatively simple score function based on a local overlap between the reads, mate-pairs long range data to resolve repeat boundary regions (through look-ahead), its relative performance and accuracy with respect to other shotgun assembly procedures, and certain test examples with the genomes of *Brucella suis Wolbachia*, and *Staphylococcus Epidermidis* as can be used in the exemplary embodiments shown in FIGS. 3-11, for example.

For example, FIG. 6 illustrates a graph of an example of *Brucella suis* contig length distributions. An exemplary contig length distribution 611 in accordance with certain exemplary embodiments of the present disclosure (herein referred to, e.g., as SUTTA), shown in the top panel 610, is compared with an example contig length distribution 621 according to another procedure (herein referred to, e.g., as MINIMUS), shown in the bottom panel 620. As can be seen, the exemplary contig length distribution 611 in accordance with certain exemplary embodiments of the present disclosure (SUTTA) can provide more efficient results than the example contig length distribution 621 according to an example of a MINIMUS procedure.

Figure 7:
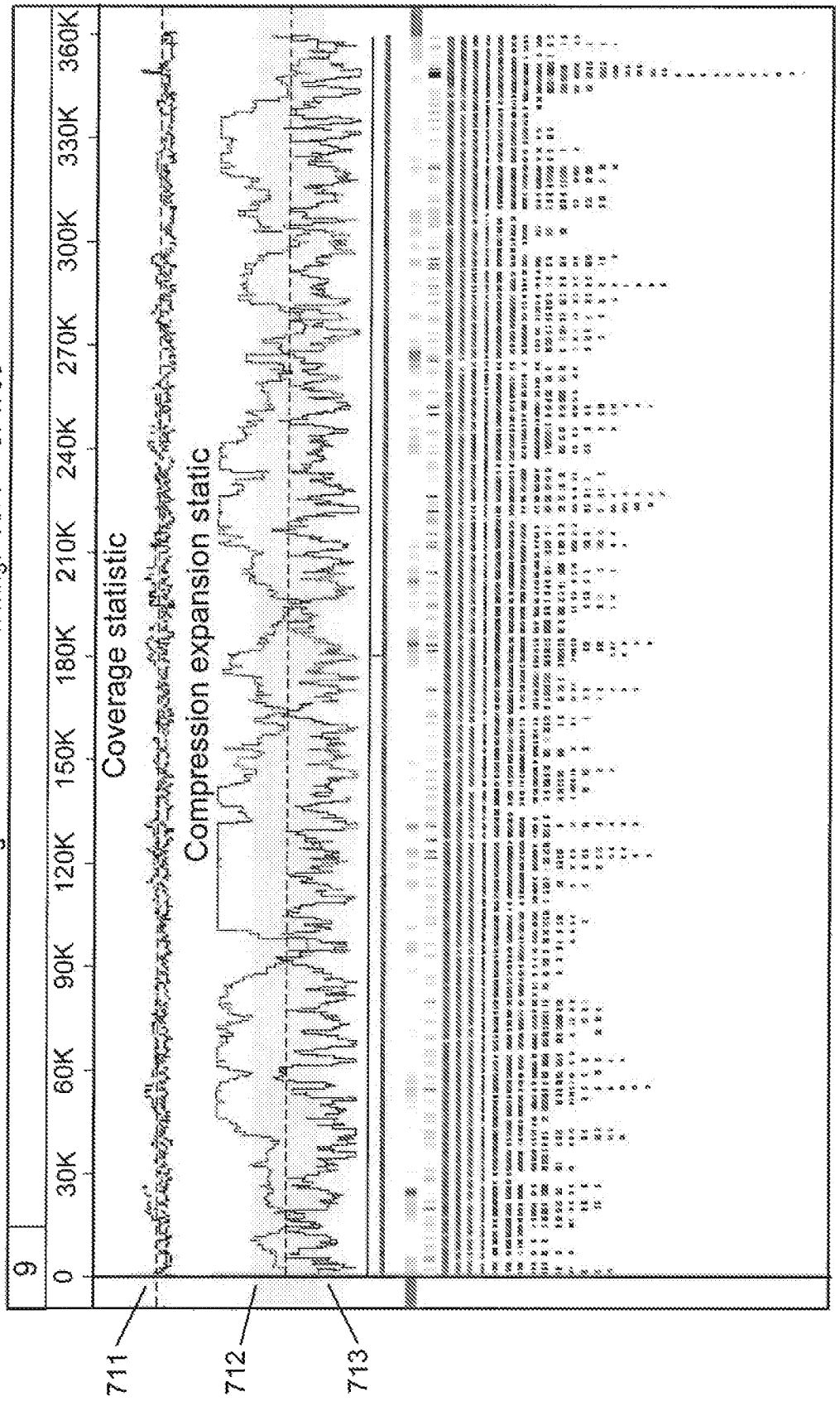
FIG. 7 is an illustration of an example of a *Brucella suis* big contig (359.5 Kbp) in accordance with an exemplary embodiment of the present disclosure.

FIG. 7 shows an example of a *Brucella suis* big contig (359.5 Kbp) in accordance with certain exemplary embodiments of the present disclosure. Exemplary coverage statistics 711 are shown near the top if the figure. Exemplary compression expansion 712 is shown directly below the exemplary coverage statistics 711, and exemplary static 713 is shown directly below the exemplary compression expansion 712.

FIG. 8 shows an example of a table 800 providing comparison of exemplary embodiments according to the present disclosure (SUTTA) and examples of five other sequence assemblers (Minimus 803, TIGR 804, CAP3 805, Euler 806, Phrap 807). Two versions according to certain exemplary embodiments of the present disclosure (SUTTA) are shown in this exemplary comparison. SUTTA$^c$ 801 can use a conservative approach, where an ambiguity encountered at a repeat boundary can be resolved by pruning the reads extending the current layout except the one with the highest overlap score. SUTTA$^a$ 802 instead can use an aggressive strategy, where, e.g., all extending reads at a repeat boundary can be expanded. As shown in table 800, there are exemplary comparisons for *Brucella suis* 810, *Walbachia* Sp. 811, *Staphylococcus epidermidis* 812, *Strptococcus suis* 813 and *Steptococcus uberis* 814.

Figure 9:
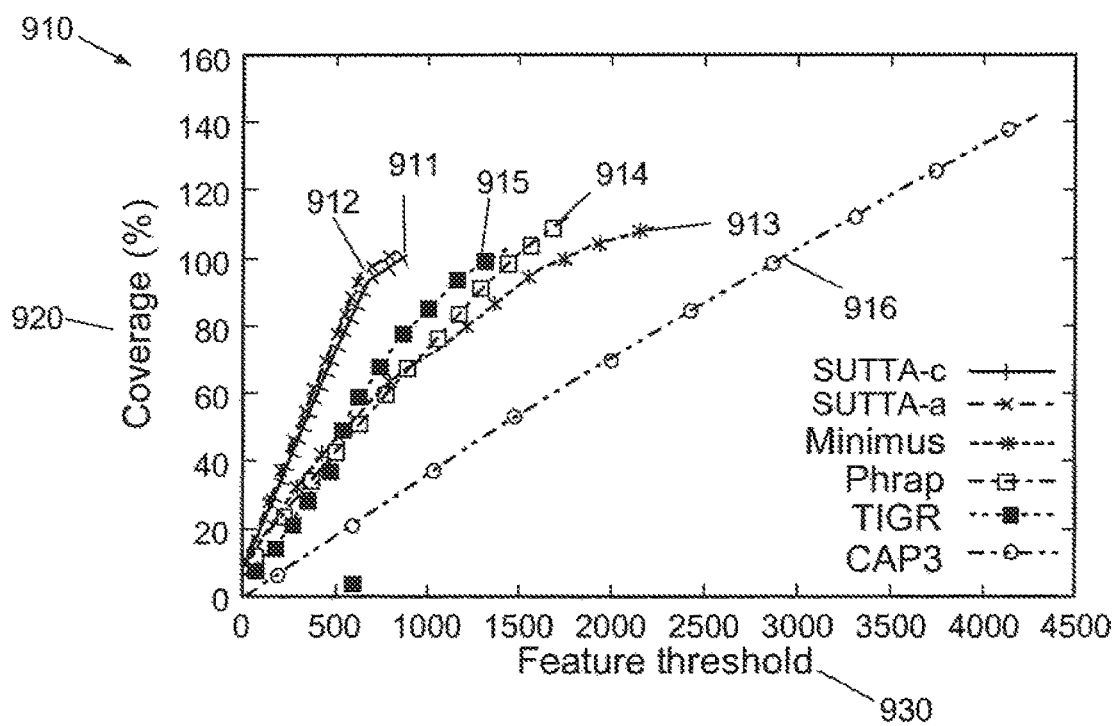
FIG. 9 is a graph of an example of a Feature-Response curve for the *Staphylococcus* genome, comparing an example in accordance with the present disclosure and four other sequence assemblers when no mate-pairs are used in the assembly.

FIG. 9 shows an exemplary graph of "Feature-Response curve" for the *Staphylococcus* genome when no mate-pairs are used in the assembly in accordance with an exemplary embodiment of the present disclosure. As shown, this exemplary Feature-Response curve 910 illustrates a comparison of results from examples of sequence assemblers SUTTA$^c$ 911, SUTTA$^a$ 912, Minimus 913, Phrap 914, TIGR 915 and CAP3 916, the comparison being based on a genome coverage 920 and a feature threshold 930.

Exemplary Feature-Response curves according to the present disclosure can be provided as a new and more reliable metric than a contig size analysis since, a contig size analysis, as illustrated in FIG. 8, for example, can provide an incomplete and often misleading view of the real performance of different assemblers. Exemplary embodiments of a Feature-Response curve can characterize the sensitivity (e.g., coverage) of a sequence assembler as a function of its discrimination threshold (e.g., number of features). An AMOS package can be used, e.g., to provide an automated assembly validation pipeline called "amosvalidate" that can analyze the output of an assembler using a variety of assembly quality metrics (or features). Examples of features can include, e.g., (M) mate-pair orientations and separations, (K) repeat content by k-mer analysis, (C) depth-of-coverage, (P) correlated polymorphism in the read alignments, and (B) read alignment breakpoints to identify structurally suspicious regions of the assembly.

According to certain exemplary embodiments of the present disclosure, after executing amosvalidate procedure on an output of an assembler, each contig can be assigned a number of features that correspond to doubtful regions of an example sequence. For example, in the case of mate-pairs checking (M), the tool can flag regions where multiple matepairs are mis-oriented or the insert coverage is low. Given an example set of features, a response (quality) of the assembler output can then be analyzed as a function of the maximum number of possible errors (features) allowed in the contigs. For example, for a fixed feature threshold $\varphi$, the contigs can be sorted by size and, starting from the longest, tallied only if their sum of features is $\leq \varphi$. For the example set of contigs shown in FIG. 9, the corresponding genome coverage 920 can be computed, leading to a single point of the Feature-Response curve.

Figure 10:
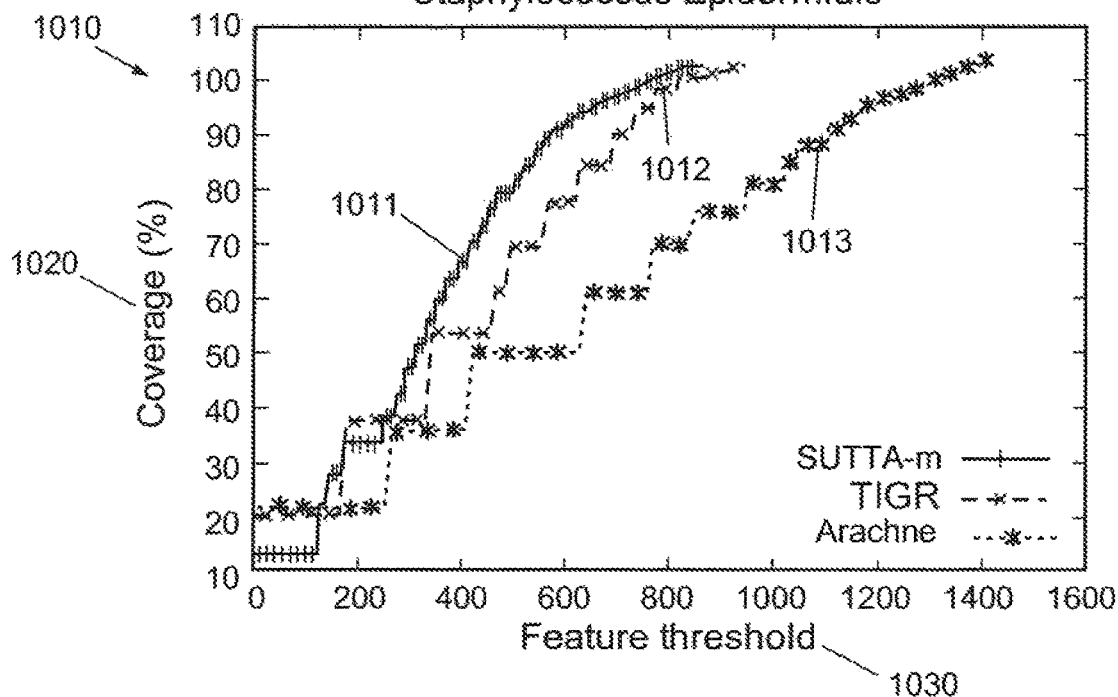
FIG. 10 is a graph of an example of a Feature-Response curve for the *Staphylococcus* genome, comparing an example in accordance with the present disclosure and other sequence assemblers when mate-pairs are used in the assembly.

FIG. 10 shows an exemplary graph of an exemplary Feature-Response curve for the *Staphylococcus* genome comparing example results from different assemblers when mate-pairs are used in an example assembly.

As shown in FIG. 10, the exemplary Feature-Response curve 1010 provides a comparison of results from examples of sequence assemblers SUTTA-m 1011 (according to an exemplary embodiment of the present disclosure), TIGR 1012 and Arachne 1013, the comparison being based on a genome coverage 1020 and a feature threshold 1030. Similarly to the example illustrated in FIG. 9, in the example illustrated in FIG. 10, and exemplary embodiment of the present disclosure (SUTTA) outperforms the assemblies from both TIGR and Arachne in terms of, e.g., assembly quality.

Figure 11A:
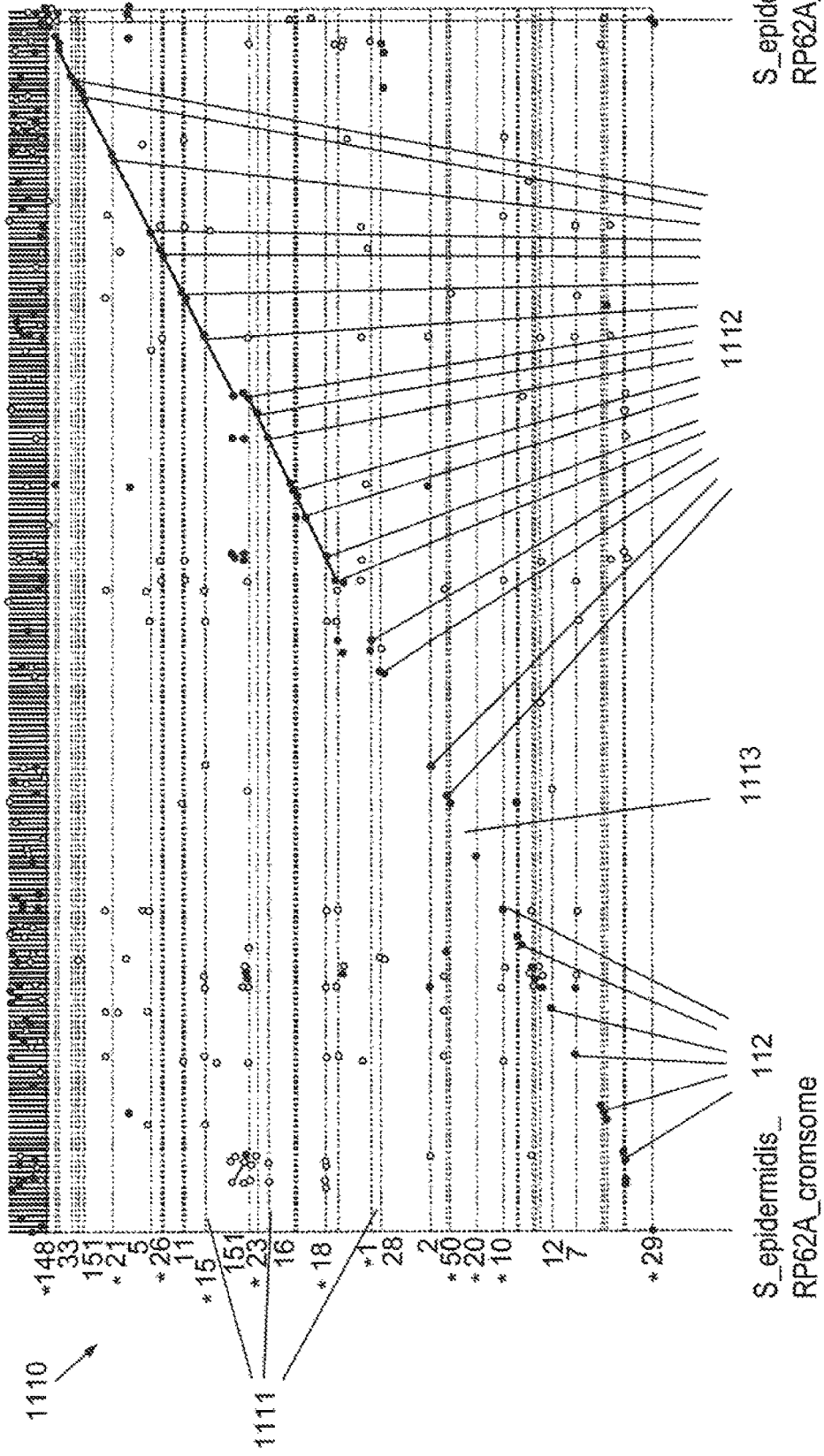
FIG. 11A is an example of dot plot alignment of the *Staphylococcus* genome assembled in accordance with an exemplary embodiment of the present disclosure.
Figure 11B:
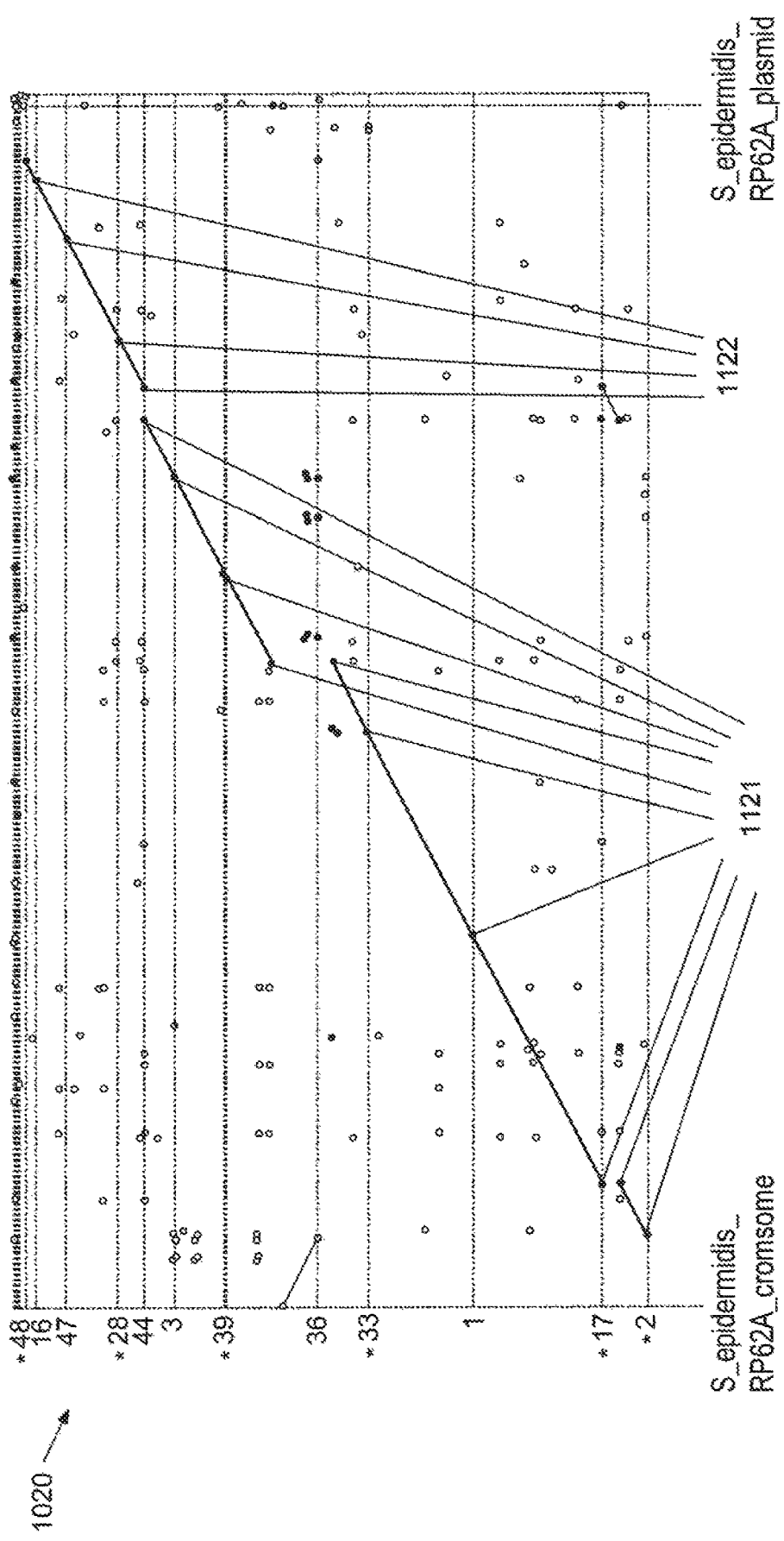
FIG. 11B is an example of dot plot alignment of the *Staphylococcus* genome assembled by another assembler.

FIG. 11A shows an example of a dot plot alignment 1110 of the *Staphylococcus* genome assembled by an exemplary embodiment in accordance with the present disclosure (SUTTA). FIG. 11B shows an example of a dot plot alignment 1120 of the *Staphylococcus* genome assembled by TIGR. The horizontal lines 1111 can indicate the boundary between assembled contigs. A comparison of FIGS. 11A and 11B illustrates that the dot plot alignment of FIG. 11A (SUTTA) outperformed.

A comparison of illustration of FIGS. 11A and 11B provides that the example SUTTA assembly in accordance with exemplary embodiments of the present disclosure shown of FIG. 11A is seen to match well with the reference sequence, having a near perfect alignment, as provided by the number of matches 1112 lying along the main diagonal 1113. In contrast, for example, TIGR shows many large assembly errors based on plots 1122, for example, many of them due to chimeric joining of segments from two distinct non-adjacent regions of the genome. Additional examples of dot plots including, for example, those for the other genomes and associated Feature-Response curves illustrated in FIGS. 9, 10 and discussed herein-above also show the example SUTTA's outperformance.

Following are certain examples of exemplary statistics determined by tests conducted in connection with an implementation according to various exemplary embodiments of the present disclosure. For example, The computational time, e.g., using a typical personal computer with a 1.8 GHz to 2.4 GHz processor, can be 20 minutes for *Brucella suis*, and can increase up to 1 hour for *Wolbachia* sp. The computational time and accuracy may be found to be significantly dependent upon the underlying queue size, for example. Because relatively higher values ues queue size can increase the computational time (e.g., because of the 0-1 law phenomena described above), optimal values for queue size can be selected to reduce complexity while maintaining the quality of the results. In addition, strong bounds on the score function can facilitate a drastic reduction of the search space (and the computational time) with a minimum loss in quality.

Exemplary embodiments of the present disclosure can be implemented using an AMOS ("A Modular Open Source whole-genome assembly") infrastructure, for example. AMOS can be used primarily for, e.g., various book-keeping facilities, software engineering features and visualization. For example, exemplary embodiments of the present disclosure can use an AMOS bank as a central data-structure consisting of a collection of indexed files comprising assembly related objects (e.g., reads, inserts, overlaps, contigs, scaffolds, etc.) to keep track of various genomic objects. Subroutines in the assembly pipeline can communicate with each other using the bank as an intermediate storage space. A relatively simple overlapper routine based on "minimizers" technique can be used to, e.g., reduce, by an order of magnitude, the number of k-mers considered in the initial phase of overlapping. Certain exemplary embodiments according to the present disclosure can use a Churchill-Waterman algorithm for, e.g., computing the consensus bases using subroutines in AMOS' consensus computation package, as it can provide a parametric implementation in the from of columns in a multiple alignment of reads, for example. The AMOS' Hawkeye visualizer can be used, for example, to facilitate inspection of large-scale assembly data, which can help to, e.g., substantially minimize the time needed to detect mis-assemblies and make accurate judgments of assembly quality. The exemplary dot-plot can be generated using the MUMmer alignment tool, for example.

The foregoing merely illustrates the principles of the present disclosure. Various modifications and alterations to the described embodiments will be apparent to those skilled in the art in view of the teachings herein. It will thus be appreciated that those skilled in the art will be able to devise, e.g., numerous systems, arrangements, computer-accessible medium and methods, which, although not explicitly shown or described herein, embody the principles of the present disclosure and are thus within the spirit and scope of the present disclosure. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. A non-transitory computer-accessible medium having stored thereon computer executable instructions for assembling at least one part of at least one of at least one haplotype sequence or at least one genotype sequence of at least one genome, wherein, when the executable instructions are executed by a computer processing arrangement, the processing arrangement is configured to perform at least one procedure comprising:

(a) obtaining (i) a plurality of randomly located short sequence reads, and (ii) overlap information about overlaps between the randomly located short sequence reads;
(b) obtaining long range information for the randomly located short sequence reads, wherein the long range information includes optical map data and mate-pair data;
(c) automatically randomly selecting a first read from the randomly located short sequence reads;
(d) automatically identifying one or more overlapping second reads of the randomly located short sequence reads that overlap with the first read;
(e) automatically generating one or more scores for the one or more overlapping second reads using the overlap information and the long range information;
(f) selecting a particular read of the one or more second overlapping reads based on the one or more scores;
(g) automatically generating a path through the plurality of randomly located short sequence reads by repeating procedures (e) and (f); and
(h) automatically assembling the at least one part of the at least one of the at least one haplotype sequence or the at least one genotype sequence of the genome based on the path.

2. The computer-accessible medium of claim 1, wherein the processing arrangement is further configured to generate the one or more scores based on at least one of a containment or an overhang among a single pair of the randomly located short sequence reads.

3. The computer-accessible medium of claim 2, wherein the processing arrangement is further configured to evaluate the at least one of the containment or the overhang using at least one of (i) an orientation of the randomly located short sequence reads, (ii) a location of the randomly located short sequence reads, or (iii) a haplotypic identity of the randomly located short sequence reads.

4. The computer-accessible medium of claim 1, wherein the processing arrangement is further configured to generate the one or more scores using a weighted transitivity score.

5. The computer-accessible medium of claim 1, wherein the processing arrangement is further configured to generate the one or more scores using a Bayesian likelihood.

6. The computer-accessible medium of claim 5, wherein the Bayesian likelihood is based on at least one penalty function.

7. The computer-accessible medium of claim 1, wherein the processing arrangement is further configured to generate the one or more scores based on a plurality of homologous reference sequences.

8. The computer-accessible medium of claim 1, wherein the processing arrangement is further configured to generate the one or more scores based on short range information.

9. The computer-accessible medium of claim 1, wherein the processing arrangement is further configured to prune at least one of the paths.

10. The computer-accessible medium of claim 9, wherein the processing arrangement is configured to prune the at least one of the paths based on the one or more scores.

11. The computer-accessible medium of claim 9, wherein the processing arrangement is configured to prune the at least one of the paths based on the overlap information.

12. The computer-accessible medium of claim 9, wherein the processing arrangement is configured to prune the at least one of the paths based on a maximum number of candidate paths allowed in a queue.

13. The computer-accessible medium of claim 12, wherein the maximum number of candidate paths allowed in the queue is fixed.

14. The computer-accessible medium of claim 9, wherein the processing arrangement is configured to prune the at least one of the paths based on a percentage of top ranking paths compared to an optimum score.

15. The computer-accessible medium of claim 14, wherein the percentage of top ranking paths compared to an optimum score dynamically changes over time.

16. The computer-accessible medium of claim 1, wherein the processing arrangement is further configured to obtain the randomly located short sequence reads using at least one of (i) Sanger chemistry, (ii) sequencing-by-synthesis, (iii) sequencing-by-hybridization, or (iv) sequencing-by-ligation.

17. The computer-accessible medium of claim 1, wherein the processing arrangement is further configured to obtain the randomly located short sequence reads using at least one method having at least one error, wherein the at least one error is at least one of: (i) incorrect base-calls, (ii) missing bases, (iii) inserted bases, or (iv) homopolymeric compression.

18. The computer-accessible medium of claim 1, wherein the long-range information further includes a physical map that is at least one of (i) an ordered restriction map, (ii) a probe map, or (iii) a base-distribution map.

19. The computer-accessible medium of claim 1, wherein the processing arrangement is further configured to evaluate the scoring procedure based on a consistency of the one or more scores with respect to the long-range information by determining a local alignment with an alignment score.

20. The computer-accessible medium of claim 1, wherein the randomly located short sequence reads are generated using at least one procedure having at least one error, and wherein the at least one error is at least one of: (i) incorrect base-calls, (ii) missing bases, (iii) inserted bases, (iv) homopolymeric compression or (v) expansion.

21. The computer-accessible medium of claim 1, wherein the long-range comprises approximately 10 Kb-200 mb of information associated with the at least one genome.

22. A method for assembling at least one part of at least one of at least one haplotype sequence or at least one genotype sequence of at least one genome, comprising:
(a) obtaining (i) a plurality of randomly located short sequence reads, and (ii) overlap information about overlaps between the randomly located short sequence reads;
(b) obtaining long range information for the randomly located short sequence reads, wherein the long range information includes optical map data and mate-pair data;
(c) automatically randomly selecting a first read from the randomly located short sequence reads;
(d) automatically identifying one or more overlapping second reads of the randomly located short sequence reads that overlap with the first read;
(e) automatically generating one or more scores regarding the one or more overlapping second reads using the overlap information and the long range information;
(f) selecting a particular read of the one or more second overlapping reads based on the one or more scores;
(g) automatically generating a path through the plurality of randomly located short sequence reads by repeating procedures (e) and (f); and
(h) using a computer hardware arrangement, automatically assembling the at least one part of the at least one of the at least one haplotype sequence or the at least one genotype sequence of the genome based on the path.

23. The method of claim 22, further comprising generating the one or more scores based on at least one of a containment or an overhang among a single pair of the randomly located short sequence reads.

24. The method of 23, further comprising evaluating the at least one of the containment or the overhang using at least one of (i) an orientation of the randomly located short sequence reads, (ii) a location of the randomly located short sequence reads, or (iii) a haplotypic identity of the randomly located short sequence reads.

25. The method of claim 22, further comprising generating the one or more scores using a weighted transitivity score.

26. The method of claim 22, further comprising generating the one or more scores using a Bayesian likelihood.

27. The method of claim 26, wherein the Bayesian likelihood is based on at least one penalty function.

28. The method of claim 22, further comprising generating the one or more scores based on a plurality of homologous reference sequences.

29. The method of claim 22, further comprising generating the one or more scores based on short range information.

30. The method of claim 22, further comprising pruning at least one of the paths.

31. The method of claim 30, further comprising pruning the at least one of the paths based on the one or more scores.

32. The method of claim 30, further comprising pruning the at least one of the paths based on the overlap information.

33. The method of claim 30, further comprising pruning the at least one of the paths based on a maximum number of candidate paths allowed in a queue.

34. The method of claim 33, wherein the maximum number of candidate paths allowed in the queue is fixed.

35. The method of claim 30, further comprising pruning the at least one of the paths based on a percentage of top ranking paths compared to an optimum score.

36. The method of claim 35, wherein the percentage of top ranking paths compared to an optimum score dynamically changes over time.

37. The method of claim 22, wherein the randomly located short sequence reads are obtained using at least one of (i) Sanger chemistry, (ii) sequencing-by-synthesis, (iii) sequencing-by-hybridization, or (iv) sequencing-by-ligation.

38. The method of claim 22, wherein the randomly located short sequence reads are obtained using at least one method having at least one error, wherein the at least one error is at least one of: (i) incorrect base-calls, (ii) missing bases, (iii) inserted bases, or (iv) homopolymeric compression.

39. The method of claim 22, wherein the long-range information further includes a physical map that is at least one of (i) an ordered restriction map, (ii) a probe map, or (iii) a base-distribution map.

40. The method of claim 22, further comprising evaluating the scoring procedure based on a consistency of the one or more scores with respect to the long-range information by determining a local alignment with an alignment score.

41. The method of claim 22, wherein the randomly located short sequence reads are generated using at least one procedure having at least one error, and wherein the at least one error is at least one of: (i) incorrect base-calls, (ii) missing bases, (iii) inserted bases, (iv) homopolymeric compression or (v) expansion.

42. The method of claim 22, wherein the long-range comprises approximately 10 Kb-200 mb of information associated with the at least one genome.

43. A system for assembling at least one part of at least one of at least one haplotype sequence or at least one genotype sequence of at least one genome, comprising:
a computer hardware arrangement configured to:
(a) obtain (i) a plurality of randomly located short sequence reads, and (ii) overlap information about overlaps between the randomly located short sequence reads;
(b) obtain long range information for the randomly located short sequence reads, wherein the long range information includes optical map data and mate-pair data;
(c) automatically randomly select a first read from the randomly located short sequence reads;
(d) automatically identify one or more overlapping second reads of the randomly located short sequence reads that overlap with the first read;
(e) automatically generate one or more scores regarding the one or more overlapping second reads using the overlap information and the long range information;
(f) select a particular read of the one or more second overlapping reads based on the one or more scores;
(g) automatically generate a path through the plurality of randomly located short sequence reads by repeating procedures (e) and (f); and
(h) automatically assemble the at least one part of the at least one of the at least one haplotype sequence or the at least one genotype sequence of the genome based on the path.

44. The system of claim 43, wherein the computer hardware arrangement is further configured to generate the one or more scores based on at least one of a containment or an overhang among a single pair of the randomly located short sequence reads.

45. The system of claim 44, wherein the computer hardware arrangement is further configured to evaluate the at least one of the containment or the overhang using at least one of (i) an orientation of the randomly located short sequence reads, (ii) a location of the randomly located short sequence reads, or (iii) a haplotypic identity of the randomly located short sequence reads.

46. The system of claim 43, wherein the computer hardware arrangement is further configured to generate the one or more scores using a weighted transitivity score.

47. The system of claim 43, wherein the computer hardware arrangement is further configured to generate the one or more scores using a Bayesian likelihood.

48. The system of claim 47, wherein the Bayesian likelihood is based on at least one penalty function.

49. The system of claim 43, wherein the computer hardware arrangement is further configured to generate the one or more scores based on a plurality of homologous reference sequences.

50. The system of claim 43, wherein the computer hardware arrangement is further configured to generate the one or more scores based on short range information.

51. The system of claim 43, wherein the computer hardware arrangement is further configured to prune at least one of the paths.

52. The system of claim 51, wherein the computer hardware arrangement is configured to prune the at least one of the paths based on the one or more scores.

53. The system of claim 51, wherein the computer hardware arrangement is configured to prune the at least one of the paths based on the overlap information.

54. The system of claim 51, wherein the computer hardware arrangement is configured to prune the at least one of the paths based on a maximum number of candidate paths allowed in a queue.

55. The system of claim 54, wherein the maximum number of candidate paths allowed in the queue is fixed.

56. The system of claim 51, wherein the computer hardware arrangement is configured to prune the at least one of the paths based on a percentage of top ranking paths compared to an optimum score.

57. The system of claim 56, wherein the percentage of top ranking paths compared to an optimum score dynamically changes over time.

58. The system of claim 43, wherein the computer hardware arrangement is further configured to obtain the randomly located short sequence reads using at least one of (i) Sanger chemistry, (ii) sequencing-by-synthesis, (iii) sequencing-by-hybridization, or (iv) sequencing-by-ligation.

59. The system of claim 43, wherein the computer hardware arrangement is further configured to obtain the randomly located short sequence reads using at least one method having at least one error, wherein the at least one error is at least one of: (i) incorrect base-calls, (ii) missing bases, (iii) inserted bases, or (iv) homopolymeric compression.

60. The system of claim 43, wherein the long-range information further includes a physical map that is at least one of (i) an ordered restriction map, (ii) a probe map, or (iii) a base-distribution map.

61. The system of claim 43, wherein the computer hardware arrangement is further configured to evaluate the scoring procedure based on a consistency of the one or more scores with respect to the long-range information by determining a local alignment with an alignment score.

62. The system of claim 43, wherein the randomly located short sequence reads are generated using at least one procedure having at least one error, and wherein the at least one error is at least one of: (i) incorrect base-calls, (ii) missing bases, (iii) inserted bases, (iv) homopolymeric compression or (v) expansion.

63. The system of claim 43, wherein the long-range comprises approximately 10 Kb-200 mb of information associated with the at least one genome.

* * * * *

UNITED STATES PATENT AND TRADEMARK OFFICE
CERTIFICATE OF CORRECTION

| | | |
|---|---|---|
| PATENT NO. | : 10,839,940 B2 | Page 1 of 1 |
| APPLICATION NO. | : 13/139809 | |
| DATED | : November 17, 2020 | |
| INVENTOR(S) | : Mishra et al. | |

It is certified that error appears in the above-identified patent and that said Letters Patent is hereby corrected as shown below:

In the Specification

Amend the Statement Regarding Federally Sponsored Research paragraph, under Column 1, Lines 18-22 with the following paragraph:

"This invention was made with government support under grant number R21 HG003714 awarded by the National Institutes of Health. Therefore, the government has certain rights in the invention."

Signed and Sealed this
Seventeenth Day of January, 2023

Katherine Kelly Vidal
*Director of the United States Patent and Trademark Office*